United States Patent
Clough et al.

(10) Patent No.: US 8,920,679 B2
(45) Date of Patent: Dec. 30, 2014

(54) FLUORINATED SILYLETHYNYL PENTACENE COMPOUNDS AND COMPOSITIONS AND METHODS OF MAKING AND USING THE SAME

(75) Inventors: Robert Steven Clough, Saint Paul, MN (US); Richard M. Flynn, Mahtomedi, MN (US); George G. I. Moore, Afton, MN (US); John E. Anthony, Lexington, KY (US); Marcia M. Payne, Lexington, KY (US)

(73) Assignees: 3M Innovative Properties Co., St Paul, DE (US); Outrider Technologies, Louisville, KY (US)

( * ) Notice: Subject to any disclaimer, the term of this patent is extended or adjusted under 35 U.S.C. 154(b) by 538 days.

(21) Appl. No.: 13/318,617

(22) PCT Filed: May 28, 2010

(86) PCT No.: PCT/US2010/036559
§ 371 (c)(1),
(2), (4) Date: Nov. 3, 2011

(87) PCT Pub. No.: WO2010/138807
PCT Pub. Date: Dec. 2, 2010

(65) Prior Publication Data
US 2012/0061620 A1     Mar. 15, 2012

Related U.S. Application Data

(60) Provisional application No. 61/182,561, filed on May 29, 2009.

(51) Int. Cl.
*H01B 1/00* (2006.01)
*H01L 29/08* (2006.01)
*H01J 1/62* (2006.01)
*C07F 7/08* (2006.01)

(52) U.S. Cl.
CPC .................................... *C07F 7/0818* (2013.01)
USPC .............................. 252/500; 257/40; 313/504

(58) Field of Classification Search
None
See application file for complete search history.

(56) References Cited

U.S. PATENT DOCUMENTS

| | | | |
|---|---|---|---|
| 6,664,354 B2 | 12/2003 | Savu | |
| 6,690,029 B1 | 2/2004 | Anthony | |
| 6,864,396 B2 | 3/2005 | Smith | |
| 7,061,010 B2 | 6/2006 | Minakata | |

(Continued)

FOREIGN PATENT DOCUMENTS

| JP | 2007-158062 | 6/2007 |
|---|---|---|
| JP | 2007-299852 | 11/2007 |

(Continued)

OTHER PUBLICATIONS

Anthony, "A Road Map to Stable, Soluble, Easily Crystallized Pentacene Derivatives", Organic Letters, Jan. 2002, vol. 4. No. 1, pp. 15-18, XP002547727.

(Continued)

*Primary Examiner* — Harold Pyon
*Assistant Examiner* — Jaison Thomas
(74) *Attorney, Agent, or Firm* — Withers & Keys, LLC

(57) ABSTRACT

Fluorinated silylethynyl pentacenes and compositions containing fluorinated silylethynyl pentacenes are disclosed. Methods of making and using fluorinated silylethynyl pentacenes and compositions containing fluorinated silylethynyl pentacenes are also disclosed.

20 Claims, 3 Drawing Sheets

(56) References Cited

U.S. PATENT DOCUMENTS

| | | | |
|---|---|---|---|
| 7,385,221 | B1 | 6/2008 | Anthony |
| 7,498,662 | B2 | 3/2009 | Napierala |
| 7,576,208 | B2 | 8/2009 | Brown |
| 7,666,968 | B2 | 2/2010 | Zhu |
| 7,842,942 | B2 * | 11/2010 | Brown et al. .................. 257/40 |
| 7,879,688 | B2 | 2/2011 | Novack |
| 2003/0116755 | A1 | 6/2003 | Takahashi |
| 2004/0222412 | A1 | 11/2004 | Bai |
| 2006/0220007 | A1 | 10/2006 | Bailey |
| 2006/0267004 | A1 | 11/2006 | Fallis |
| 2007/0102696 | A1 | 5/2007 | Brown |
| 2007/0114516 | A1 | 5/2007 | Napierala |
| 2007/0137520 | A1 | 6/2007 | Brown |
| 2007/0146426 | A1 | 6/2007 | Nelson |
| 2009/0001356 | A1 | 1/2009 | Novack |
| 2010/0270542 | A1 | 10/2010 | Zhu |
| 2011/0073813 | A1 * | 3/2011 | Caldwell et al. ............. 252/500 |

FOREIGN PATENT DOCUMENTS

| | | | |
|---|---|---|---|
| WO | 2005055248 | | 6/2005 |
| WO | 2006119853 | | 11/2006 |
| WO | 2006125504 | | 11/2006 |
| WO | 2007078860 | | 7/2007 |
| WO | 2007082584 | | 7/2007 |
| WO | 2008107089 | | 9/2008 |
| WO | 2008128618 | | 10/2008 |
| WO | WO 2009109273 A1 * | 9/2009 | ............. H01L 51/00 |
| WO | 2009155106 | | 12/2009 |
| WO | 2009158201 | | 12/2009 |

OTHER PUBLICATIONS

Anthony, "Functionalized Acenes and Heteroacenes for Organic Electronics", Chemical Reviews, Dec. 2006, vol. 106, No. 12, pp. 5028-5048.

Bernard, "Double Diels—Alder Strategies to Soluble 2,9- and 2,9,6,13-Tetraethynylpentacenes, Photolytic [4 + 4] Cycloadditions, and Pentacene Crystal Packing", Journal of Organic Chemistry, Sep. 14, 2007, vol. 72, No. 19, pp. 7729-7236, XP002547732.

Chen, "Morphology and Molecular Orientation of Thin-film Bis(triisopropylsilylethynyl) Pentacene", Journal of Materials Research, Jun. 2007, vol. 22, No. 6, pp. 1701-1709.

Gundlach, "Contact-induced Crystallinity for High-performance Soluble Acene-based Transistors and Circuits", Nature Materials, Mar. 2008, vol. 7, No. 3, pp. 216-221.

Jiang, "Design, Synthesis, and Properties of New Derivatives of Pentacene", Journal of Organic Chemistry, Mar. 3, 2006, vol. 71, No. 5, pp. 2155-2158, XP002547731.

Kim, "High-mobility Organic Transistors Based on Single-Crystalline Microribbons of Triisopropylsilylethynyl Pentacene via Solution-phase Self-Assembly", Advanced Materials, Mar. 2007, vol. 19, No. 5, pp. 678-682. XP002547726.

Lehnherr, "Pentacene Oligomers and Polymers: Functionalization of Pentacene to Afford Mono-, Di-, Tri-, and Polymeric Materials", Organic Letters, Oct. 25, 2007, vol. 9, No. 22, pp. 4583-4586, XP002547733.

Palayangoda, "Synthesis of Highly Soluble and Oxidatively Stable Tetraceno[2,3-b]thiophenes and Pentacenes", Journal of Organic Chemistry, Aug. 17, 2007, vol. 72, No. 17, pp. 6584-6587.

Park, "High Mobility Solution Processed 6,13-bis(triisopropylsilylethynyl) Pentacene Organic Thin Film Transistors", Applied Physics Letters, 2007, vol. 91, Issue 6, pp. 063514-1-063514-3.

Payne, "Robust, Soluble Pentacene Ethers", Organic Letters, May 13, 2004, vol. 6, No. 10, pp. 1609-1612, XP002547728.

Payne, "Stable, Crystalline Acenedithiophenes with up to Seven Linearly Fused Rings", Organic Letters, Sep. 16, 2004, vol. 6, No. 19, pp. 3325-3328.

Payne, "Organic Field-Effect Transistors from Solution-Deposited Functionalized Acenes with Mobilities as High as 1 cm2/V•s", Journal of the American Chemical Society, Apr. 13, 2005, vol. 127, No. 14, 4986-4987.pp.

Payne, "Functionalized Higher Acenes: Hexacene and Heptacene", Journal of the American Chemical Society, Jun. 8, 2005, vol. 127, No. 22, pp. 8028-8029, XP002547730.

Swartz, "Synthesis and Characterization of Electron-Deficient Pentacenes", Organic Letters, Jul. 21, 2005, vol. 7, No. 15, pp. 3163-3166.

Wobkenberg, "Low-voltage Organic Transistors Based on Solution Processed Semiconductors and Self-assembled Monolayer Gate Dielectrics", Applied Physics Letters, 2008, vol. 93, Issue 1, pp. 013303-1-013303-3.

International Search Report for PCT/US2010/036559, 3 pages.

International Search Report for PCT/US2009/045667.

Okamoto, "Synthesis of Solution-Soluble Pentacene-Containing Conjugated Copolymers", Journal of the American Chemical Society, Aug. 29, 2007, vol. 129, No. 34, pp. 10308-10309, XP002547734.

Kaur, et al. "Exploiting Substituent Effects for the Synthesis of a Photooxidatively Resistant Heptacene Derivative", J. Am. Chem. Soc. vol. 131, pp. 3424-3425, 2009.

Lim et al., "Control of the Morphology and Structural Development of Solution-Processed Functionalized Acenes of High-Performance Organic Transistor", Adv. Funct. Materials, vol. 19, pp. 1515-1525, 2009.

Qingxin, et al., "Organic Transistors of Small Molecular Weight Materials", Progress in Chemistry, vol. 18, No. 11, pp. 1540-1553, 2006.

* cited by examiner

FLUORINATED SILYLETHYNYL PENTACENE COMPOUNDS AND COMPOSITIONS AND METHODS OF MAKING AND USING THE SAME

The present application is a national phase patent application corresponding to International Patent Application Serial No. PCT/US2010/036559 entitled "FLUORINATED SILYLETHYNYL PENTACENE COMPOUNDS AND COMPOSITIONS AND METHODS OF MAKING AND USING THE SAME" and filed on 28 May 2010, and claims the benefit of priority to U.S. Provisional Patent Application Ser. No. 61/182,561 filed on 29 May 2009 and entitled "FLUORINATED SILYLETHYNYL PENTACENE COMPOUNDS AND COMPOSITIONS AND METHODS OF MAKING AND USING THE SAME."

FIELD OF THE INVENTION

The present invention is related generally to fluorinated silylethynyl pentacenes and compositions containing fluorinated silylethynyl pentacenes. The present invention is further related generally to methods of making and using fluorinated silylethynyl pentacenes, as well as compositions containing fluorinated silylethynyl pentacenes.

BACKGROUND OF THE INVENTION

Electronic devices composed of organic-based transistors can typically be manufactured at lower cost and applied to a larger area format when compared with their inorganic counterparts. However, the performance of organic-based transistors has typically been lower. In general, organic-based transistors utilize either small molecules or polymers as the semiconductor material. Typically, small molecule semiconductor materials have low solubility in organic solvents and thus typically require a vacuum deposition method to form films. Shadow mask or photolithographic methods are usually required to pattern multiple layers in order to make useful devices. Vacuum deposition and lithography often require processes that cost much more than processes that do not usually require vacuum deposition and lithography (e.g., solution coating methods).

One cost effective approach of producing inexpensive electronic devices is to apply an organic semiconductor material by any of the following exemplary coating processes: spin coating, knife-coating, roll-to-roll web-coating, and dip coating, as well as printing processes such as ink-jet printing, screen printing, and offset lithography. However, as discussed above, many organic semiconductor materials are notoriously insoluble in solvents and those that are soluble are generally unstable in solution. Due to insolubility and instability concerns, the ability to apply many organic semiconductor materials using the above-mentioned inexpensive coating steps to form inexpensive electronic devices is limited.

Some organic semiconductors based on pentacene with 6,13-silylethynyl substitution have been shown to (i) be soluble in organic solvents, (ii) be stable in solution, and (iii) provide good performance in organic field effect transistors (OFETs). For example, 6,13-bis[(triisopropylsilanyl)ethynyl]pentacene (i.e., also referred to as 6,13-bis[(triisopropylsilyl)-ethynyl]pentacene and referred to herein as "TIPS-pentacene") has been shown to (i) have a degree of solubility in organic solvents, (ii) have a degree of stability when in solution, and (iii) provide good performance in organic field effect transistors (OFETs). However, even TIPS-pentacene provides limited solubility in some organic solvents, as well as limited performance in electronic devices, for example, as measured in terms of charge carrier mobility values.

In addition, many known pentacene compounds have one or more of the following shortcomings: (i) a limited ability to wet a surface, (ii) a limited degree of hydrophobicity and/or oleophobicity, (iii) a limited degree of resistance to oxidation, and (iv) limited photochemical stability.

SUMMARY OF THE INVENTION

The present invention addresses some of the problems in the art by the discovery of organic compounds, namely, pentacene compounds with 6,13-silylethynyl substitution, having one or more of the following properties: (i) enhanced solubility in one or more organic solvents (e.g., fluorinated solvents), (ii) enhanced stability when incorporated into a given organic solvent (e.g., fluorinated solvents), (iii) enhanced ability to wet a surface, (iv) enhanced hydrophobicity and/or oleophobicity, (v) enhanced resistance to oxidation, (vi) enhanced performance when incorporated into an electronic device as a semiconductor layer as measured by the charge carrier mobility value of the electronic device, (vii) enhanced performance when incorporated into an electronic device as a semiconductor layer as measured by the energy conversion efficiency of the electronic device, and (viii) enhanced performance when incorporated into an electronic device as a semiconductor layer as measured by the stability of the electronic characteristics of the device over time in the environment. The pentacene compounds of the present invention may be utilized in coatable compositions in the production of electronic devices and other coated substrates.

The present invention is directed to pentacene compounds with specific 6,13-silylethynyl substitution. In one exemplary embodiment, the present invention is directed to pentacene compounds having a chemical structure:

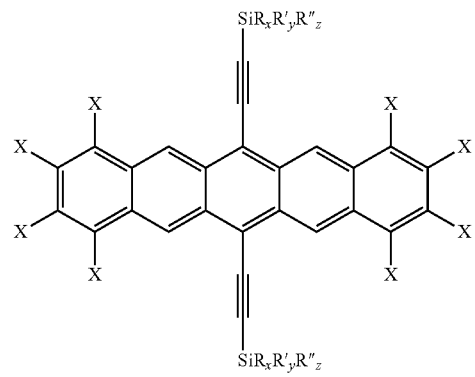

(also referred to hereinafter as "Structure A")

wherein:
each R, R' and R" independently comprises (i) hydrogen, (ii) a branched or unbranched, substituted or unsubstituted alkyl group, (iii) a branched or unbranched, substituted or unsubstituted alkenyl group, (iv) a substituted or unsubstituted cycloalkyl group, (v) a substituted or unsubstituted cycloalkylalkylene group, (vi) a branched or unbranched, substituted or unsubstituted alkynyl group, (vii) a substituted or unsubstituted aryl group, (viii) a substituted or unsubstituted arylalkylene group, (ix) an acetyl group, (x) a substituted or unsubstituted heterocyclic ring comprising at least one of O, N, S and Se in the ring, (xi) a substituted or unsubstituted ether group or polyether group, or (xii) a substituted or unsubstituted sulfonamide group; and at least one of R, R' and R" is present and comprises a fluorinated monovalent radical comprising the branched or unbranched substituted alkyl group, the branched or unbranched substituted alkenyl group, the substituted cycloalkyl group, the substituted cycloalkylalkylene group, the branched or unbranched substituted alkynyl group, the substituted aryl group, the substituted arylalkylene group, the substituted heterocyclic ring comprising at least one of O, N, S and Se in the ring, the substituted ether group or polyether group, or the substituted sulfonamide group, wherein the fluorinated monovalent radical comprises one or more fluorine atoms with the one or more fluorine atoms being separated from both silicon atoms by at least three atoms or at least four covalent bonds;

x, y and z each independently equal 0, 1, 2 or 3;
(x+y+z)=3; and
each X independently comprises (i) hydrogen, (ii) a halogen, (iii) a branched or unbranched, substituted or unsubstituted alkyl group, (iv) a substituted or unsubstituted aryl group, (v) a branched or unbranched, substituted or unsubstituted alkenyl group, (vi) a branched or unbranched, substituted or unsubstituted alkynyl group, (vii) a cyano group, (viii) a nitro group, (ix) a branched or unbranched, substituted or unsubstituted alkoxy group, or (x) any two adjacent X groups combine to form (a) a substituted or unsubstituted carbocyclic ring or (b) a substituted or unsubstituted heterocyclic ring.

The present invention is further directed to compositions comprising (I) at least one pentacene compound having Structure A, wherein R, R', R", x, y, z and X are as described above; and (II) a solvent. The compositions of the present invention may comprise at least one pentacene compound and solvent alone or in combination with one or more additional composition components, such as a polymer additive, rheological modifier, a surfactant, or any combination thereof.

The present invention is even further directed to a substrate having at least one coatable surface and a coated layer on the at least one coatable surface, wherein the coated layer comprises a pentacene compound having Structure A, wherein R, R', R", x, y, z and X are as described above. In one exemplary embodiment, the substrate comprises an electronic device or an electronic device component.

The present invention is also directed to methods of making pentacene compounds having Structure A, wherein R, R', R", x, y, z and X are as described above.

The present invention is further directed to methods of using one or more pentacene compounds to form compositions (e.g., ink jet printable compositions), coatings, substrates having a coated layer thereon, electronic device components, and electronic devices, wherein at least one pentacene compound has Structure A, wherein R, R', R", x, y, z and X are as described above.

These and other features and advantages of the present invention will become apparent after a review of the following detailed description of the disclosed embodiments and the appended claims.

BRIEF DESCRIPTION OF THE DRAWINGS

The present invention is further described with reference to the appended figures, wherein.

DETAILED DESCRIPTION OF THE INVENTION

Figure 1:
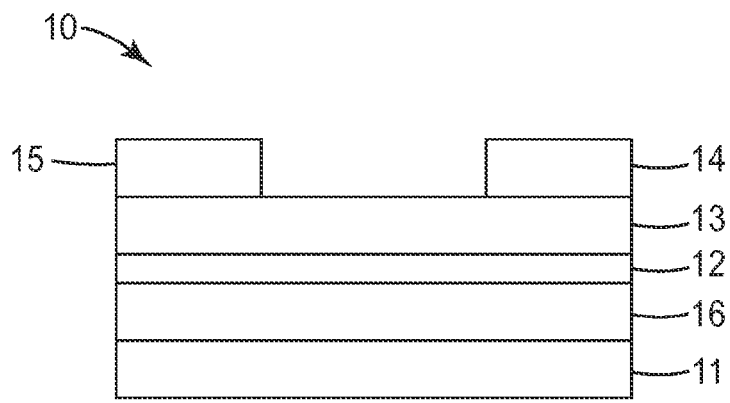
FIG. 1 is a cross-sectional view of an exemplary thin film transistor comprising a semiconductor layer formed via solution deposition of a composition containing at least one fluorinated pentacene compound of the present invention.

The present invention is directed to fluorinated pentacene compounds having a chemical structure (also referred to herein as "Structure A"):

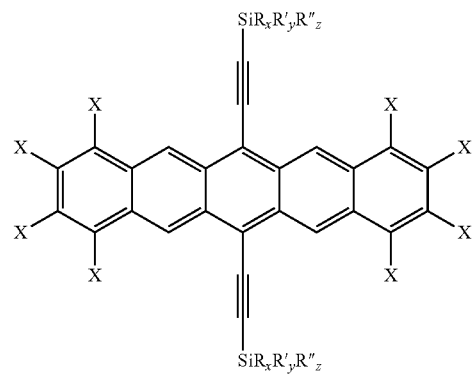

wherein:
each R, R' and R" independently comprises (i) hydrogen, (ii) a branched or unbranched, substituted or unsubstituted alkyl group, (iii) a branched or unbranched, substituted or unsubstituted alkenyl group, (iv) a substituted or unsubstituted cycloalkyl group, (v) a substituted or unsubstituted cycloalkylalkylene group, (vi) a branched or unbranched, substituted or unsubstituted alkynyl group, (vii) a substituted or unsubstituted aryl group, (viii) a substituted or unsubstituted arylalkylene group, (ix) an acetyl group, (x) a substituted or unsubstituted heterocyclic ring comprising at least one of O, N, S and Se in the ring, (xi) a substituted or unsubstituted ether group or polyether group, or (xii) a substituted or unsubstituted sulfonamide; and at least one of R, R' and R" is present and comprises a fluorinated monovalent radical comprising the branched or unbranched substituted alkyl group, the branched or unbranched substituted alkenyl group, the substituted cycloalkyl group, the substituted cycloalkylalkylene group, the branched or unbranched substituted alkynyl group, the substituted aryl group, the substituted arylalkylene group, the substituted heterocyclic ring comprising at least one of O, N, S and Se in the ring, the substituted ether group or polyether group, or the substituted sulfonamide group, wherein the fluorinated monovalent radical comprises one or more fluorine atoms with the one or more fluorine atoms being separated from both silicon atoms by at least three atoms or at least four covalent bonds;

x, y and z each independently equal 0, 1, 2 or 3;
(x+y+z)=3; and
each X independently comprises (i) hydrogen, (ii) a halogen, (iii) a branched or unbranched, substituted or unsubstituted alkyl group, (iv) a substituted or unsubstituted aryl group, (v) a branched or unbranched, substituted or unsubstituted alkenyl group, (vi) a branched or unbranched, substituted or unsubstituted alkynyl group, (vii) a cyano group, (viii) a nitro group, (ix) a branched or unbranched, substituted or unsubstituted alkoxy group, or (x) any two adjacent X groups combine to form (a) a substituted or unsubstituted carbocyclic ring or (b) a substituted or unsubstituted heterocyclic ring.

A number of terms are used to describe the pentacene compounds of the present invention. As used herein, the various terms are defined as follows:

"Alkyl group" refers to a monovalent group that is a radical of an alkane, which is a saturated hydrocarbon. The alkyl can be linear, branched, cyclic, or combinations thereof and typically contains 1 to 30 carbon atoms. In some embodiments, the alkyl group contains 4 to 30, 1 to 20, 4 to 20, 1 to 14, 1 to 10, 4 to 10, 4 to 8, 1 to 8, 1 to 6, or 1 to 4 carbon atoms. Examples of alkyl groups include, but are not limited to, methyl, ethyl, n-propyl, iso-propyl, n-butyl, tert-butyl, iso-butyl, n-pentyl, n-hexyl, cyclohexyl, n-octyl, n-heptyl, and ethylhexyl.

"Substituted alkyl group" refers to an alkyl group having one or more substituents thereon, wherein each of the one or more substituents comprises a monovalent moiety containing one or more atoms other than carbon and hydrogen either alone (e.g., a halogen such as F) or in combination with carbon (e.g., a cyano group) and/or hydrogen atoms (e.g., a hydroxyl group or a carboxylic acid group).

"Alkenyl group" refers to a monovalent group that is a radical of an alkene, which is a hydrocarbon with at least one carbon-carbon double bond. The alkenyl can be linear, branched, cyclic, or combinations thereof and typically contains 2 to 30 carbon atoms. In some embodiments, the alkenyl contains 2 to 20, 2 to 14, 2 to 10, 4 to 10, 4 to 8, 2 to 8, 2 to 6, or 2 to 4 carbon atoms. Exemplary alkenyl groups include, but are not limited to, ethenyl, propenyl, and butenyl.

"Substituted alkenyl group" refers to an alkenyl group having (i) one or more C—C double bonds, and (ii) one or more substituents thereon, wherein each of the one or more substituents comprises a monovalent moiety containing one or more atoms other than carbon and hydrogen either alone (e.g., a halogen such as F) or in combination with carbon (e.g., a cyano group) and/or hydrogen atoms (e.g., a hydroxyl group or a carboxylic acid group).

"Alkynyl group" refers to a monovalent group that is a radical of an alkyne, a hydrocarbon with at least one carbon-carbon triple bond. The alkynyl can be linear, branched, cyclic, or combinations thereof and typically contains 2 to 30 carbon atoms. In some embodiments, the alkynyl contains 2 to 20, 2 to 14, 2 to 10, 4 to 10, 4 to 8, 2 to 8, 2 to 6, or 2 to 4 carbon atoms. Exemplary alkynyl groups include, but are not limited to, ethynyl, propynyl, and butynyl.

"Substituted alkynyl group" refers to an alkynyl group having (i) one or more C—C triple bonds, and (ii) one or more substituents thereon, wherein each of the one or more substituents comprises a monovalent moiety containing one or more atoms other than carbon and hydrogen either alone (e.g., a halogen such as F) or in combination with carbon (e.g., a cyano group) and/or hydrogen atoms (e.g., a hydroxyl group or a carboxylic acid group or a silyl group).

"Cycloalkyl group" refers to a monovalent group that is a radical of a ring structure consisting of 3 or more carbon atoms in the ring structure (i.e., only carbon atoms in the ring structure and one of the carbon atoms of the ring structure is the radical).

"Substituted cycloalkyl group" refers to a cycloalkyl group having one or more substituents thereon, wherein each of the one or more substituents comprises a monovalent moiety containing one or more atoms (e.g., a halogen such as F, an alkyl group, a cyano group, a hydroxyl group, or a carboxylic acid group).

"Cycloalkylalkylene group" refers to a monovalent group that is a ring structure consisting of 3 or more carbon atoms in the ring structure (i.e., only carbon atoms in the ring), wherein the ring structure is attached to an acyclic alkyl group (typically, from 1 to 3 carbon atoms, more typically, 1 carbon atom) and one of the carbon atoms of the acyclic alkyl group is the radical.

"Substituted cycloalkylalkylene group" refers to a cycloalkylalkylene group having one or more substituents thereon, wherein each of the one or more substituents comprises a monovalent moiety containing one or more atoms (e.g., a halogen such as F, an alkyl group, a cyano group, a hydroxyl group, or a carboxylic acid group).

"Aryl group" refers to a monovalent group that is a radical of an aromatic carbocyclic compound. The aryl can have one aromatic ring or can include up to 5 carbocyclic ring structures that are connected to or fused to the aromatic ring. The other ring structures can be aromatic, non-aromatic, or combinations thereof. Examples of aryl groups include, but are not limited to, phenyl, biphenyl, terphenyl, anthryl, naphthyl, acenaphthyl, anthraquinonyl, phenanthryl, anthracenyl, pyrenyl, perylenyl, and fluorenyl.

"Substituted aryl group" refers to an aryl group having one or more substituents on the ring structure, wherein each of the one or more substituents comprises a monovalent moiety containing one or more atoms (e.g., a halogen such as F, an alkyl group, a cyano group, a hydroxyl group, or a carboxylic acid group).

"Arylalkylene group" refers to a monovalent group that is an aromatic ring structure consisting of 5 to 10 carbon atoms in the ring structure (i.e., only carbon atoms in the ring structure), wherein the aromatic ring structure is attached to an acyclic alkyl group having one or more carbon atoms (typically, from 1 to 3 carbon atoms, more typically, 1 carbon atom) and one of the carbons of the acyclic alkyl group is the radical.

"Substituted arylalkylene group" refers to an arylalkylene group having one or more substituents thereon, wherein each of the one or more substituents comprises a monovalent moiety containing one or more atoms (e.g., a halogen such as F, an alkyl group, a cyano group, a hydroxyl group, or a carboxylic acid group).

"Acetyl group" refers to a monovalent radical having the formula —C(O)CH$_3$.

"Heterocyclic ring" refers to a saturated, partially saturated, or unsaturated ring structure comprising at least one of O, N, S and Se in the ring structure.

"Substituted heterocyclic ring" refers to a heterocyclic ring having one or more substituents bonded to one or more members of the ring structure, wherein each of the one or more substituents comprises a monovalent moiety containing one or more atoms (e.g., a halogen such as F, an alkyl group, a cyano group, a hydroxyl group, or a carboxylic acid group).

"Carbocyclic ring" refers to a saturated, partially saturated, or unsaturated ring structure comprising only carbon in the ring structure.

"Substituted carbocyclic ring" refers to a carbocyclic ring having one or more substituents bonded to one or more members of the ring structure, wherein each of the one or more substituents comprises a monovalent moiety containing one or more atoms (e.g., a halogen such as F, an alkyl group, a cyano group, a hydroxyl group, or a carboxylic acid group).

"Ether group" refers to a —$R_a$—O—$R_b$ radical wherein $R_a$ is a branched or unbranched alkylene, arylene, alkylarylene or arylalkylene hydrocarbon and $R_b$ is a branched or unbranched alkyl, aryl, alkylaryl or arylalkyl hydrocarbon.

"Substituted ether group" refers to an ether group having one or more substituents thereon, wherein each of the one or more substituents comprises a monovalent moiety containing one or more atoms other than carbon and hydrogen either alone (e.g., a halogen such as F) or in combination with carbon (e.g., a cyano group) and/or hydrogen atoms (e.g., a hydroxyl group or a carboxylic acid group).

"Polyether group" refers to a —$(R_a—O)_m$—$R_b$ radical wherein $R_a$ and $R_b$ are as defined above, and m is an integer greater than 1.

"Substituted polyether group" refers to a polyether group having one or more substituents thereon, wherein each of the one or more substituents comprises a monovalent moiety containing one or more atoms other than carbon and hydrogen either alone (e.g., a halogen such as F) or in combination with carbon (e.g., a cyano group) and/or hydrogen atoms (e.g., a hydroxyl group or a carboxylic acid group).

"Sulfonamide group" refers to a —$R_a$—N($R_c$)S(O)$_2$—$R_b$ radical wherein each $R_a$ and $R_b$ are as defined above, and each $R_c$ is independently a hydrogen, or branched or unbranched alkyl, aryl, alkylaryl or arylalkyl hydrocarbon.

"Substituted sulfonamide group" refers to a sulfonamide group having one or more substituents thereon, wherein each of the one or more substituents comprises a monovalent moiety containing one or more atoms other than carbon and hydrogen either alone (e.g., a halogen such as F) or in combination with carbon (e.g., a cyano group) and/or hydrogen atoms (e.g., a hydroxyl group or a carboxylic acid group).

"Alkoxy group" refers to a monovalent group of formula —OR where R is an alkyl group. Examples include, but are not limited to, methoxy, ethoxy, propoxy, and butoxy.

"Substituted alkoxy group" refers to an alkoxy group having one or more substituents thereon, wherein each of the one or more substituents comprises a monovalent moiety containing one or more atoms other than carbon and hydrogen either alone (e.g., a halogen such as F) or in combination with carbon (e.g., a cyano group) and/or hydrogen atoms (e.g., a hydroxyl group or a carboxylic acid group).

"Charge carrier mobility value" refers to the drift velocity of a charge carrier (cm/s) per unit applied field (V/cm) with resulting measurement units of "cm$^2$/V-s" as measured using any test method for measuring the drift velocity of a charge carrier.

Fluorinated pentacene compounds having the above chemical structure have been found to possess at least one of the following properties: (i) enhanced solubility in one or more organic solvents (e.g., fluorinated solvents), (ii) enhanced stability when incorporated into a given organic solvent (e.g., fluorinated solvents), (iii) enhanced ability to wet a surface, (iv) enhanced hydrophobicity and/or oleophobicity, (v) enhanced resistance to oxidation, (vi) enhanced performance when incorporated into an electronic device as a semiconductor layer as measured by the charge carrier mobility value of the electronic device, (vii) enhanced performance when incorporated into an electronic device as a semiconductor layer as measured by the energy conversion efficiency of the electronic device, and (viii) enhanced performance when incorporated into an electronic device as a semiconductor layer as measured by the stability of the electronic characteristics of the device over time in the environment. By varying the R groups (i.e., R, R' and R") and X groups in the above chemical structure, one can tailor a resulting pentacene compound for a given application (e.g., as a semiconductor layer in an electronic device).

For example, when a given fluorinated pentacene compound of the present invention is to be used to form a semiconductor layer in an electronic device, the ability of the fluorinated pentacene compound to exhibit two-dimensional stacking (i.e., 2-D stacking of individual molecules) is an important consideration, which significantly impacts the charge carrier mobility value of the resulting semiconductor layer. The dimensionality of a given stacking configuration may be easily measured by examination of the single-crystal X-ray structure of a given material. A given material exhibiting two-dimensional, or "brickwork" stacking is characterized by having four nearest neighbors with contacts between aromatic carbon atoms lying roughly within the van der Waals radius of carbon (ideally, 3.3-3.6 Å). Considering a simple pentacene unit, any material that has two aromatic close-contact neighbors above the plane of the pentacene ring, and two aromatic close-contact neighbors below the plane of the pentacene ring is typically classified as having two-dimensional interactions or 2-D stacking. A common alternative case is one-dimensional stacking, where there is only one close-contact neighbor above and below the plane of the pentacene ring. It is generally the case that molecules with two-dimensional pi-stacking yield superior thin-film morphologies for field-effect transistor applications, along with improved charge transport in the solid state. Similarly, materials with one-dimensional pi-stacking tend to exhibit superior performance in photovoltaic devices, whether used as the electron donor component or the acceptor component. The fluorinated pentacene compounds of the present invention can be modified to exhibit either 1-D or 2-D stacking.

In some exemplary embodiments, the fluorinated pentacene compounds have Structure A wherein one or more fluorinated monovalent radicals are present and each fluorinated monovalent radical independently comprises a branched or unbranched substituted alkyl group, a branched or unbranched substituted alkenyl group, a substituted cycloalkyl group, a substituted cycloalkylalkylene group, a branched or unbranched substituted alkynyl group, a substituted aryl group, a substituted arylalkylene group, a substituted heterocyclic ring comprising at least one of O, N, S and Se in the ring, a substituted ether group or polyether group, or a substituted sulfonamide group, and each fluorinated monovalent radical comprises one or more fluorine atoms with the one or more fluorine atoms being separated from both silicon atoms of the pentacene compound (as shown in Structure A) by at least three atoms (or, for example, any number of atoms greater than three and up to about eighteen atoms) or at least four covalent bonds (or, for example, any number of covalent bonds greater than four and up to about nineteen covalent bonds).

In some exemplary embodiments, each fluorinated monovalent radical independently comprises (i) a branched or unbranched substituted alkyl group (e.g., a fluorinated C3-C18 alkyl group), (ii) a branched or unbranched substituted alkenyl group (e.g., a fluorinated C3-C18 alkenyl group), (iii) a substituted cycloalkyl group, (iv) a substituted cycloalkylalkylene group, (v) a branched or unbranched substituted alkynyl group (e.g., a fluorinated C3-C18 alkynyl group), (vi) a substituted aryl group, or (vii) a substituted arylalkylene group, wherein the one or more fluorine atoms of a given fluorinated monovalent radical are separated from both silicon atoms of the pentacene compound (as shown in Structure A) by at least three atoms or at least four covalent bonds.

In some exemplary embodiments, the fluorinated pentacene compounds have Structure A wherein at least one fluorinated monovalent radical comprises the formula:

wherein $R_f$ is a partially (i.e., contains one or more hydrogen atoms) or completely fluorinated (i.e., contains no hydrogen atoms) alkyl group, typically, a C1-C16 alkyl group. The fluorinated alkyl group $R_f$ is branched, unbranched, acyclic, cyclic, or a combination thereof. The asterisk indicates the attachment location to the silicon atom in Structure A.

In some exemplary embodiments, the fluorinated pentacene compounds have Structure A wherein at least one fluorinated monovalent radical comprises the formula:

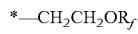

wherein $R_f$ is as described above. The asterisk indicates the attachment location to the silicon atom in Structure A.

In some exemplary embodiments, the fluorinated pentacene compounds have Structure A wherein at least one fluorinated monovalent radical comprises the formula:

wherein $R_f$ is as described above, and o is an integer of 1 or greater, typically ranging from 1 to 5. The asterisk indicates the attachment location to the silicon atom in Structure A.

In some exemplary embodiments, the fluorinated pentacene compounds have Structure A wherein at least one fluorinated monovalent radical comprises the formula:

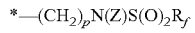

wherein $R_f$ is as described above, p is an integer of 2 or greater, typically ranging from 2 to 5, and Z represents —H, —CH$_3$, or —CH$_2$CH$_3$. The asterisk indicates the attachment location to the silicon atom in Structure A.

In some exemplary embodiments, the fluorinated pentacene compounds have Structure A wherein at least one fluorinated monovalent radical comprises the formula:

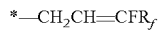

wherein $R_f$ is as described above. The asterisk indicates the attachment location to the silicon atom in Structure A.

In some exemplary embodiments, the fluorinated pentacene compounds have Structure A wherein at least one fluorinated monovalent radical comprises the formula:

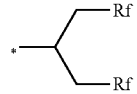

wherein each $R_f$ is independently a partially (i.e., contains one or more hydrogen atoms) or completely fluorinated (i.e., contains no hydrogen atoms) alkyl group having up to about ten carbon atoms (or up to about four carbon atoms). The asterisk indicates the attachment location to the silicon atom in Structure A.

In some exemplary embodiments, the fluorinated pentacene compounds have Structure A wherein at least one fluorinated monovalent radical comprises the formula:

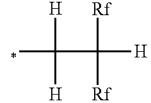

wherein each $R_f$ is independently a partially (i.e., contains one or more hydrogen atoms) or completely fluorinated (i.e., contains no hydrogen atoms) alkyl group having up to about ten carbon atoms (or up to about four carbon atoms). The asterisk indicates the attachment location to the silicon atom in Structure A.

In some exemplary embodiments, the fluorinated pentacene compounds have Structure A wherein at least one fluorinated monovalent radical comprises the formula:

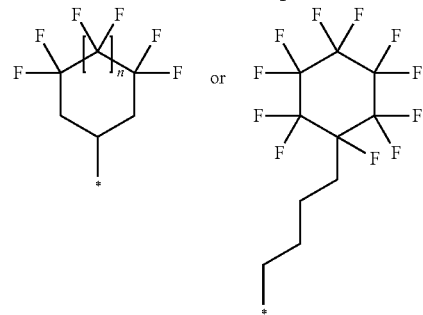

wherein n=0 or 1 or 2 or 3. The asterisk indicates the attachment location to the silicon atom in Structure A.

In some embodiments, one of R, R' and R" is present and comprises a fluorinated monovalent radical as described herein, and the remaining groups from R, R' and R" comprise identical or different moieties. Although one or more of the remaining groups from R, R' and R" can comprise hydrogen, more typically, the remaining groups from R, R' and R" each independently comprise monovalent radicals other than hydrogen. For example, in some embodiments, one of R, R' and R" is present and comprises a fluorinated monovalent radical as described herein, and the remaining groups from R, R' and R" each independently comprise identical or different branched or unbranched alkyl groups, more typically, identical branched or unbranched alkyl groups.

Some exemplary fluorinated pentacene compounds having the above-described structures are shown below:

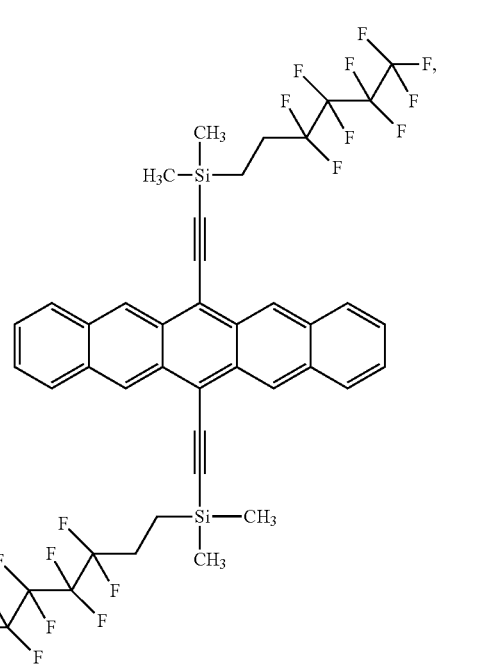

-continued
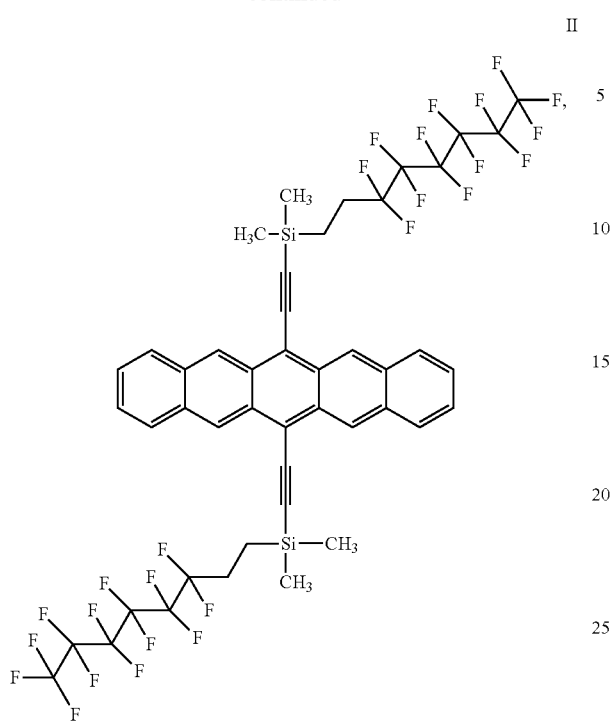
II
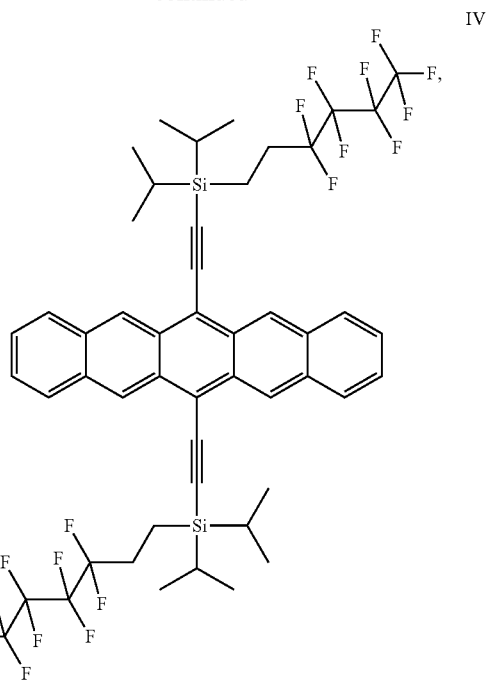
IV
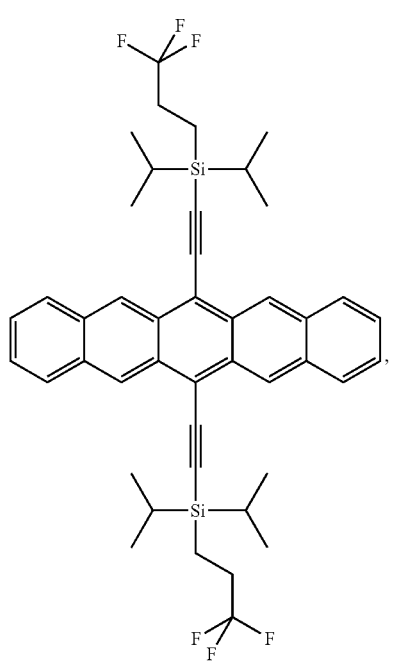
III
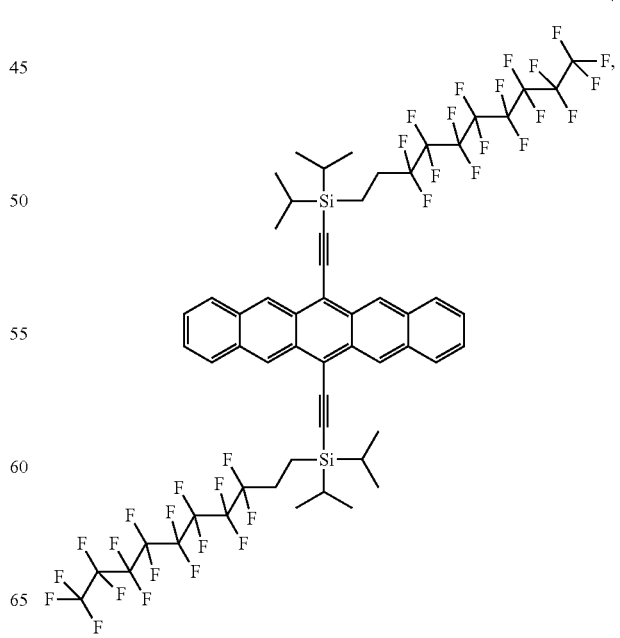
V

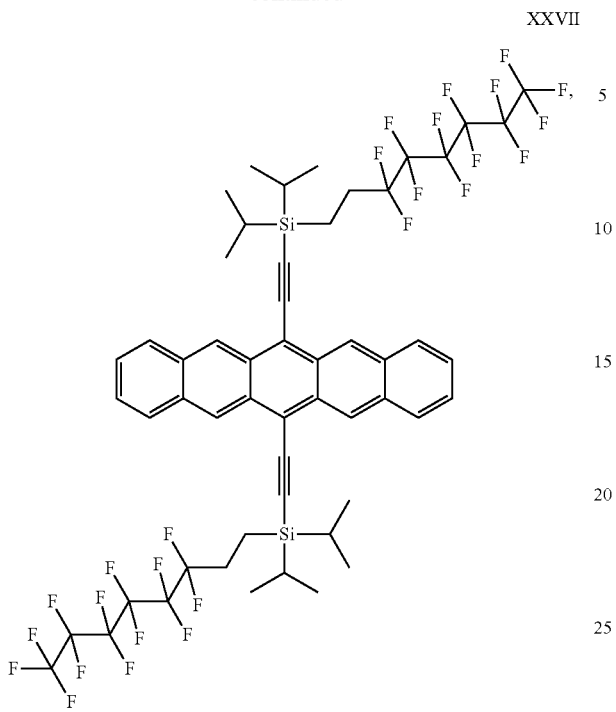

XXVII

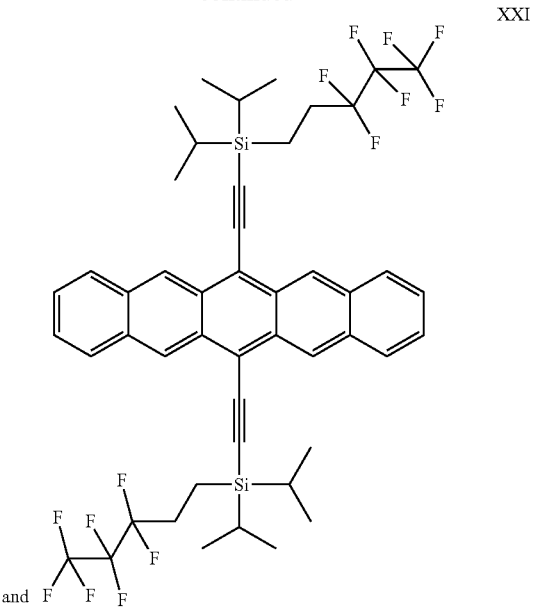

XXI

XX wherein:

I=6,13-bis(3,3,4,4,5,5,6,6,6-nonafluorohexyldimethylsilylethynyl)pentacene;

II=6,13-bis(3,3,4,4,5,5,6,6,7,7,8,8,8-tridecafluorooctyldimethylsilylethynyl)pentacene;

III=6,13-bis(3,3,3-trifluoropropyldiisopropylsilylethynyl)pentacene;

IV=6,13-bis(3,3,4,4,5,5,6,6,6-nonafluorohexyldiisopropylsilylethynyl)pentacene;

V=6,13-bis(3,3,4,4,5,5,6,6,7,7,8,8,9,9,10,10,10-heptadecafluorodecyldiisopropylsilylethynyl)pentacene;

XXVII=6,13-bis(3,3,4,4,5,5,6,6,7,7,8,8,8-tridecafluorooctyldiisopropylsilylethynyl)pentacene;

XX=6,13-bis((3,3,4,4,5,5,6,6,7,7,8,8,9,10,10,10-hexadecafluoro-9-trifluoromethyldecyl)-diisopropylsilylethynyl)pentacene; and XXI=6,13-bis(3,3,4,4,5,5,5-heptafluoropentyldiisopropylsilylethynyl)pentacene.

In some embodiments, one of R, R' and R'' is present and comprises a fluorinated monovalent radical as described herein, and the remaining R groups each independently comprise identical or different branched or unbranched alkylene groups, more typically, identical branched or unbranched alkylene groups. For example, in each of exemplary compounds III, IV, V, XX, XXI and XXVII described above, the isopropyl radical may be replaced with an isopropenyl radical.

In other exemplary embodiments, the fluorinated pentacene compounds have Structure A wherein one or more fluorinated monovalent radicals are present and at least one fluorinated monovalent radical (i) comprises a substituted heterocyclic ring comprising at least one of O, N, S and Se in the ring, a substituted ether group or polyether group, or a substituted sulfonamide group, (ii) comprises one or more fluorine atoms with the one or more fluorine atoms being separated from both silicon atoms of the pentacene compound (as shown in Structure A) by at least three atoms or at least four covalent bonds, and (iii) at least one atom of the at least three atoms (i.e., the at least three atoms separating any fluorine atom from both silicon atoms shown in Structure A) comprises an atom other than carbon. For example, in some exemplary embodiments, at least one atom of the at least three atoms comprises nitrogen or sulfur as in a sulfonamide group. For example, in some exemplary embodiments, at least one atom of the at least three atoms comprises oxygen.

Exemplary fluorinated pentacene compounds having such structures are provided below:

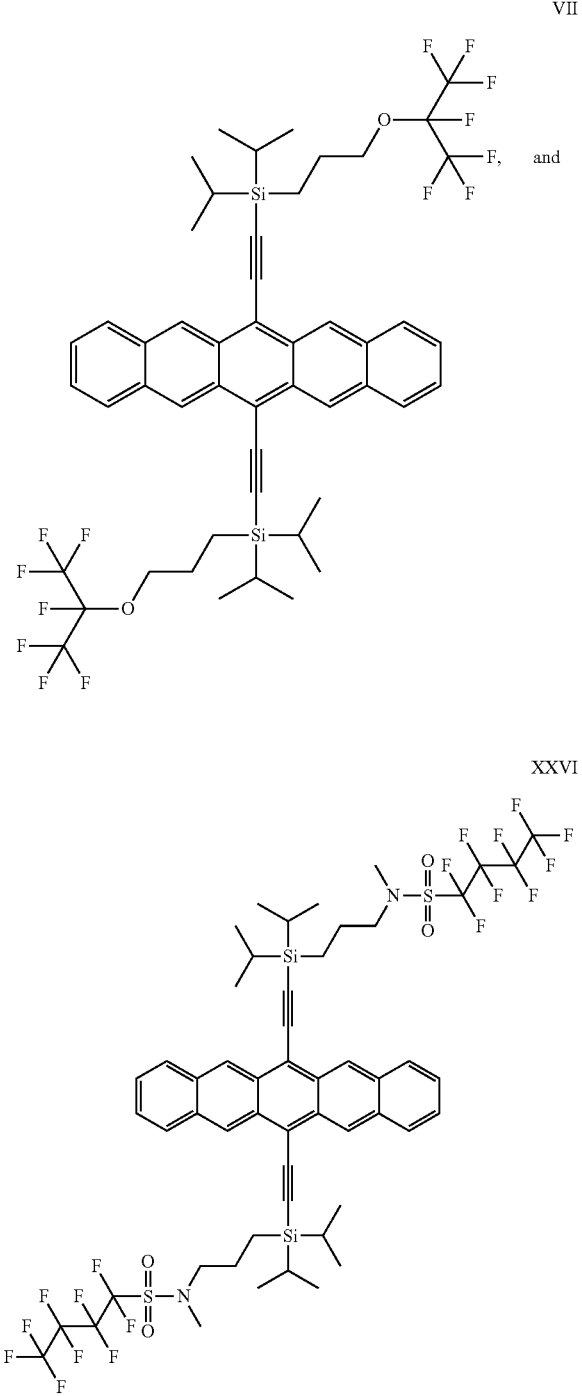 [SMILES: CC(C)[Si](C#Cc1c2cc3ccccc3cc2c(C#C[Si](CCCOC(F)(C(F)(F)F)C(F)(F)F)(C(C)C)C(C)C)c2cc3ccccc3cc12)(CCCOC(F)(C(F)(F)F)C(F)(F)F)C(C)C ; CC(C)[Si](C#Cc1c2cc3ccccc3cc2c(C#C[Si](CCCN(C)S(=O)(=O)C(F)(F)C(F)(F)C(F)(F)C(F)(F)F)(C(C)C)C(C)C)c2cc3ccccc3cc12)(CCCN(C)S(=O)(=O)C(F)(F)C(F)(F)C(F)(F)C(F)(F)F)C(C)C]

wherein:

VII=6,13-bis((3-heptafluoroisopropoxy)propyldiisopropyl-silylethynyl)pentacene; and XXVI=6,13-bis((N-methyl-nonafluorobutylsulfonamidopropyl)diisopropylsilylethynyl)-pentacene.

In some exemplary embodiments, the fluorinated pentacene compounds have Structure A wherein R, R' and R" together comprise (i) at least one fluorinated monovalent radical, such as one or more of the herein-described fluorinated monovalent radicals, in combination with (ii) at least one C1 to C8 alkyl group, (iii) at least one C3 to C8 cycloalkyl group, (iv) at least one C2 to C8 alkenyl group, or (v) a C1 to C8 alkyl group in combination with a C3 to C8 cycloalkyl group or a C2 to C8 alkenyl group. In other exemplary embodiments, the fluorinated pentacene compounds have Structure A wherein R, R' and R" together comprise (i) one fluorinated monovalent radical, such as one or more of the herein-described fluorinated monovalent radicals, in combination with (ii) two C1 to C8 alkyl groups, (iii) two C3 to C8 cycloalkyl groups (e.g., two cyclopropyl groups or two cyclobutyl groups or two cyclopentyl groups), or (iv) two C2 to C8 alkenyl groups.

In some exemplary embodiments, the fluorinated pentacene compounds have Structure A wherein R, R' and R" together comprise (i) at least one fluorinated monovalent radical, such as one or more of the herein-described fluorinated monovalent radicals, in combination with (ii) at least one isopropyl group, (iii) at least one isopropenyl group, or (iv) an isopropyl group and an isopropenyl group. In other exemplary embodiments, the fluorinated pentacene compounds have Structure A wherein R, R' and R" together comprise (i) at least one fluorinated monovalent radical, such as one or more of the herein-described fluorinated monovalent radicals, in combination with (ii) at least one isopropyl group. In other exemplary embodiments, the fluorinated pentacene compounds have Structure A wherein R, R' and R" together comprise (i) at least one fluorinated monovalent radical, such as one or more of the herein-described fluorinated monovalent radicals, in combination with (ii) at least one isopropenyl group.

In some exemplary embodiments, the fluorinated pentacene compounds have Structure A wherein z=0 (i.e., at least two groups attached to the silicon atom are the same) and R, R' and R" together comprise (i) one fluorinated monovalent radical, such as one or more of the herein-described fluorinated monovalent radicals, in combination with (ii) two isopropyl groups or two isopropenyl groups.

As shown above, many of the fluorinated pentacene compounds of the present invention comprise fluorinated pentacene compounds having Structure A wherein z=0 (i.e., at least two groups attached to the silicon atom are the same). Other exemplary fluorinated pentacene compounds of the present invention wherein z=0 (i.e., at least two groups attached to the silicon atom are the same) are provided in Table 1 below.

TABLE 1

Exemplary Fluorinated Pentacene Compounds Where z = 0

| Compound | x equals: | y equals: | R is: | R' is: |
|---|---|---|---|---|
| VI | 2 | 1 | isopropyl | 3,4,4,5,5,6,6,6-octafluorohex-2-enyl |
| VIII | 2 | 1 | isopropyl | N-methyl-nonafluorobutylsulfonamidoethyl |
| IX | 1 | 2 | isopropyl | 3,3,4,4,4-pentafluorobutyl |
| X | 2 | 1 | cyclopropyl | 3,3,4,4,5,5,6,6,7,7,8,8,8-tridecafluorooctyl |
| XI | 2 | 1 | benzyl | 3,3,4,4,5,5,6,6,7,7,8,8,8-tridecafluorooctyl |
| XII | 2 | 1 | 2,3-dimethylcyclopropyl | 3,3,4,4,5,5,6,6,7,7,8,8,8-tridecafluorooctyl |
| XIII | 2 | 1 | isopropenyl | 3,3,4,4,5,5,6,6,7,7,8,8,8-tridecafluorooctyl |
| XIV | 2 | 1 | cyclobutyl | 3,3,4,4,5,5,6,6,7,7,8,8,9,9,10,10,10-heptadecafluorodecyl |
| XV | 2 | 1 | allyl | 3,3,4,4,5,5,6,6,7,7,8,8,9,9,10,10,10-heptadecafluorodecyl |
| XVI | 2 | 1 | methyl | (pentafluorophenyl)propyl |
| XVII | 2 | 1 | isopropyl | (pentafluorophenyl)propyl |
| XVIII | 2 | 1 | ethyl | 4-(trifluoromethyl)phenyl |
| XIX | 1 | 2 | allyl | 4-(undecafluorocyclohexyl)butyl |
| XXVIII | 2 | 1 | isopropenyl | 3,3,4,4,5,5,6,6,6-nonafluorohexyl |
| XXIX | 2 | 1 | cyclopropyl | 3,3,4,4,5,5,6,6,6-nonafluorohexyl |
| XXX | 2 | 1 | isopropenyl | 3,3,4,4,5,5,6,6,7,7,8,8,9,9,10,10,10-heptadecafluorodecyl |
| XXXI | 2 | 1 | cyclopropyl | 3,3,4,4,5,5,6,6,7,7,8,8,9,9,10,10,10-heptadecafluorodecyl |
| XXXII | 2 | 1 | methyl | N-methyl-nonafluorobutylsulfonamidopropyl |
| XXXIII | 2 | 1 | isopropyl | 3,4,4,5,5,6,6,7,7,8,8,8-dodecafluorooct-2-enyl |

Although not shown in Table 1, it should be noted that other fluorinated pentacene compounds of the present invention may have Structure A, wherein at least one R group attached to the silicon atom comprises a substituted or unsubstituted heterocyclic ring comprising at least one of O, N, S and Se in the ring, such as a substituted or unsubstituted furanyl group, a substituted or unsubstituted pyrrolyl group, a substituted or unsubstituted thienyl group, or a substituted or unsubstituted selenophenyl group.

In any of the above-described exemplary fluorinated pentacene compounds, one or more of R, R' and/or R" may be substituted with one or more substituents. Suitable substituents for the above-described R, R', and/or R" groups include, but are not limited to, halogens, hydroxyl groups, alkyl groups, cyano groups, amino groups, carbonyl groups, alkoxy groups, thioalkoxy groups, nitro groups, carboxylic acid groups, carboxylic ester groups, alkenyl groups, alkynyl groups, aryl groups, heteroaryl groups, or combinations thereof. Typical substituents for alkyl groups, alkenyl groups, alkynyl groups, ether groups, and sulfonamide groups include, but are not limited to, —F, —OH, —OCH$_3$, —CN, and —COOH. Typical substituents for cycloalkyl groups, cycloalkylalkylene groups, aryl groups, arylalkylene groups, acetyl groups, and heterocyclic rings (i.e., aromatic and non-aromatic heterocyclic rings) comprising at least one of O, N, S and Se in the ring include, but are not limited to, alkyl groups, —F, —OH, —OCH$_3$, —CN, and —COOH.

Further, in any of the above-described exemplary fluorinated pentacene compounds, the pentacene ring may further comprise one or more of the above-described substituents X. One or more substituents X may be utilized to further tailor a given pentacene compound for a given application. For example, one or more substituents X may be utilized to provide one or more additional benefits: (1) further enhance the ability of a given pentacene compound to exhibit two-dimensional stacking; (2) enhance the solubility of a given pentacene in certain solvents (e.g., fluorinated solvents); (3) diminish the solubility of a given pentacene in certain solvents (e.g., non-fluorinated solvents); (4) enhance the thermal resistance of a given pentacene; (5) enhance the oxidative resistance of a certain pentacene in solution or in the solid state; and (6) alter the morphology of blends of a given pentacene with polymers or other semiconductors.

In some exemplary embodiments, the fluorinated pentacene compounds of the present invention, including any of the above-described pentacene compounds, further comprise one or more substituents X, wherein each X independently comprises (i) hydrogen, (ii) a halogen, or (iii) a branched or unbranched, substituted or unsubstituted alkyl group. Exemplary substituents X include, but are not limited to, (i) fluorine, (ii) an alkyl group (e.g., a methyl group), or (iii) a perfluoroalkyl group (e.g., a trifluoromethyl group).

In some exemplary embodiments, the fluorinated pentacene compounds of the present invention, including any of the above-described pentacene compounds, further comprise one or more substituents X, wherein at least one X comprises a halogen, desirably, fluorine. In some exemplary embodiments, the fluorinated pentacene compounds of the present invention, including any of the above-described pentacene compounds, further comprise one or more substituents X, wherein at least one X comprises a branched or unbranched, substituted or unsubstituted alkyl group, such as a methyl group or a trifluoromethyl group.

In some exemplary embodiments, the fluorinated pentacene compounds of the present invention, including any of the above-described pentacene compounds, further comprise one or more substituents X, wherein at least two adjacent X groups combine to form (a) a substituted or unsubstituted carbocyclic ring or (b) a substituted or unsubstituted heterocyclic ring. In some embodiments, two adjacent X groups combine to form a substituted or unsubstituted, non-aromatic, 5 to 7 member ring fused to either terminal ring of the pentacene core, where the ring is carbocyclic or includes 1 or 2 heteroatoms selected from oxygen, nitrogen, sulfur, or selenium.

Some exemplary fluorinated pentacene compounds wherein one or more substituents X are other than —H (hydrogen) include, but are not limited to, the following compounds:

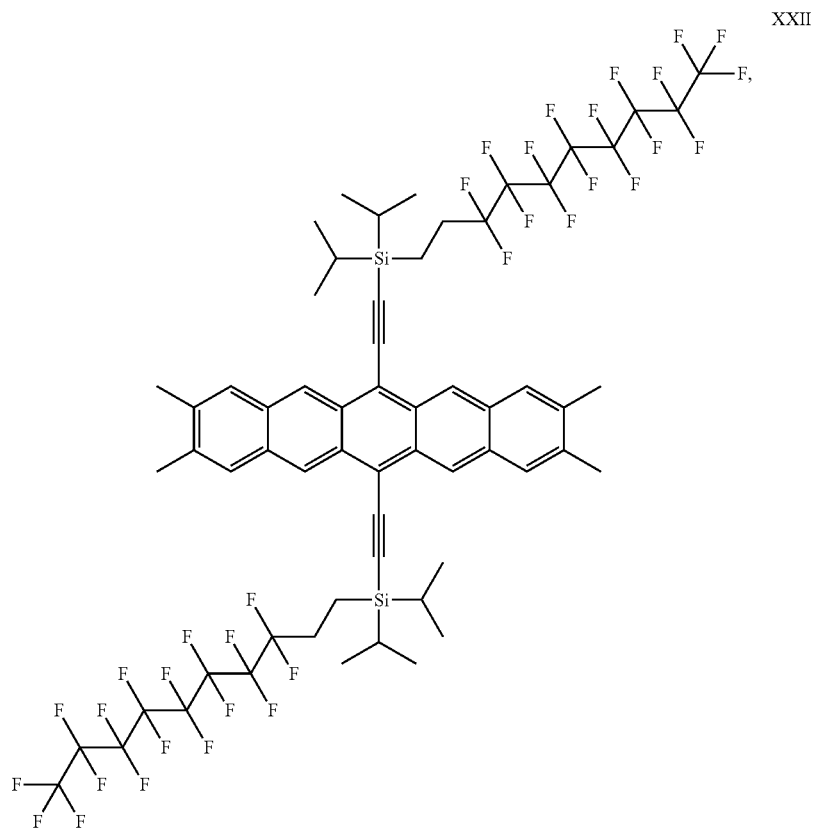

XXII

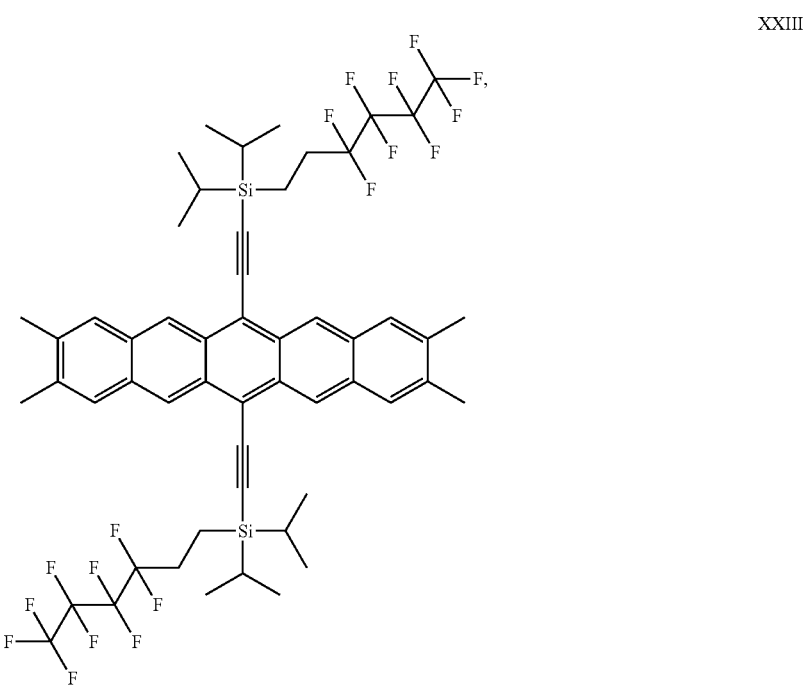

XXIII

-continued

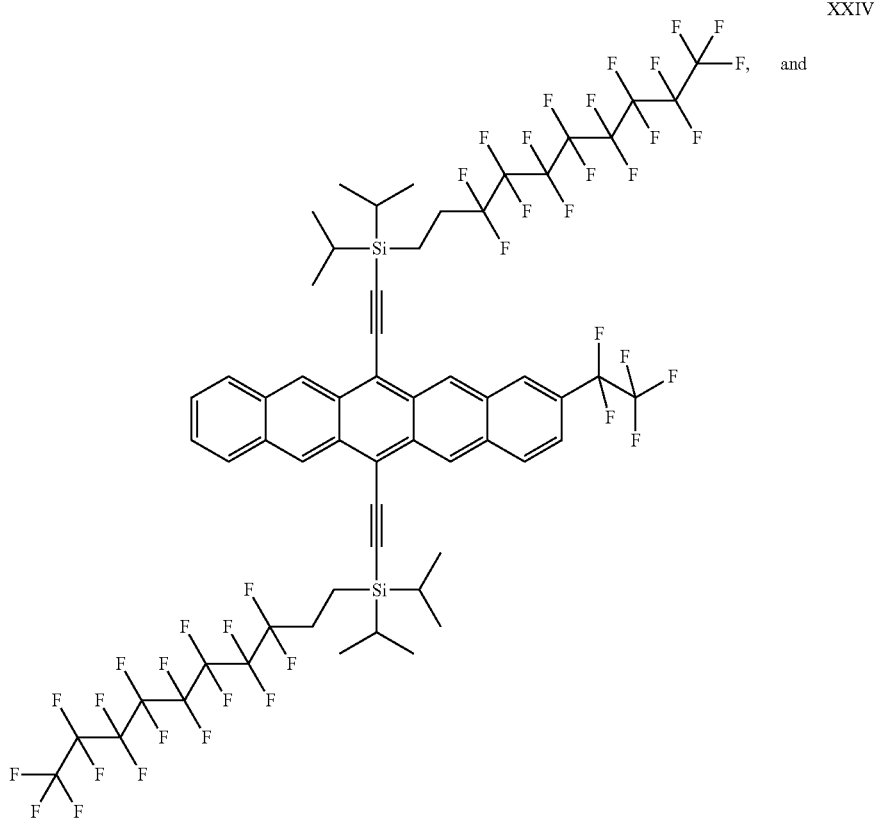

XXIV

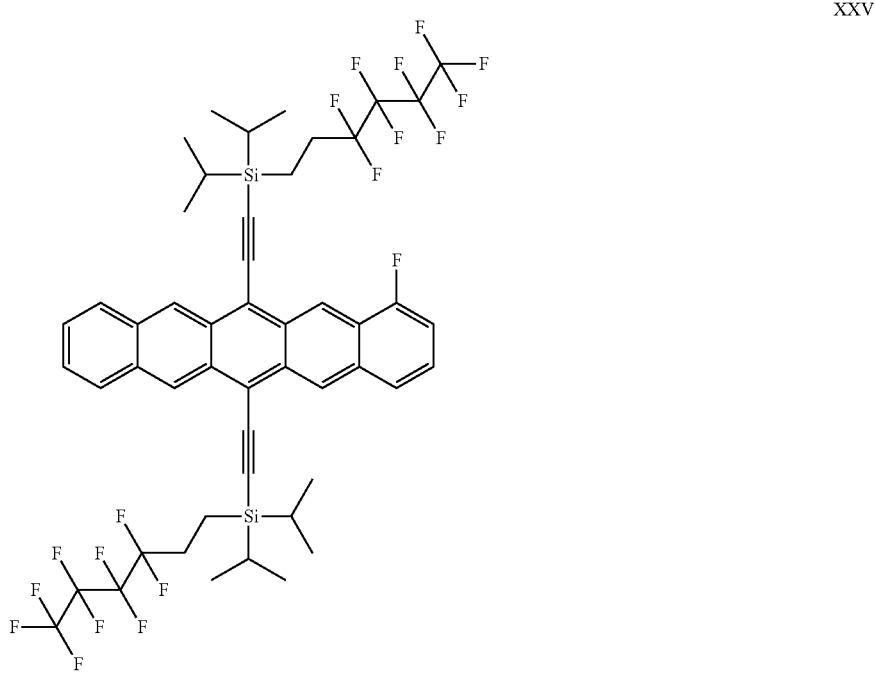

XXV wherein:
XXII=6,13-bis(3,3,4,4,5,5,6,6,7,7,8,8,9,9,10,10,10-heptadecafluorodecyldiisopropylsilylethynyl)-2,3,9,10-tetramethylpentacene;
XXIII=6,13-bis(3,3,4,4,5,5,6,6,6-nonafluorohexyldiisopropylsilylethynyl)-2,3,9,10-tetramethylpentacene;
XXIV=6,13-bis(3,3,4,4,5,5,6,6,7,7,8,8,9,9,10,10,10-heptadecafluorodecyldiisopropylsilylethynyl)-2-pentafluoroethylpentacene; and
XXV=6,13-bis(3,3,4,4,5,5,6,6,6-nonafluorohexyldiisopropylsilylethynyl)-1-fluoropentacene.

The present invention is further directed to compositions comprising (I) one or more of the above-described fluorinated pentacene compounds, and (II) a solvent. Typical solvents suitable for forming compositions of the present invention include, but are not limited to, organic solvents such as ketones, aromatic hydrocarbons, fluorinated solvents, and the like. Suitable solvents include, but are not limited to, toluene, ethylbenzene, butylbenzene, chlorobenzene, dichlorobenzene, tetrahydrofuran, isophorone, anisole, tetrahydronaphthalene, butylcyclohexane, and cyclohexanone. Solvent blends may also be utilized. Suitable solvent blends include, but are not limited to, anisole blended with decane, and butylbenzene blended with decane.

In one exemplary embodiment, the composition comprises one or more of the above-described fluorinated pentacene compounds, and a fluorinated solvent such as hexafluorobenzene, octafluorotoluene, (trifluoromethyl)benzene, 1,3-bis(trifluoromethyl)-benzene, 1,3,5-tris(trifluoromethyl)benzene, (trifluoromethoxy)benzene, 3-(trifluoromethyl)anisole, 2,3,4,5,6-pentafluoroanisole, 2,3,5,6-tetrafluoroanisole, pentafluorobenzonitrile, 2,3,4,5,6-pentafluorotoluene, 2,2,2-trifluoroacetophenone, 2',4',5'-trifluoroacetophenone, 2'-(trifluoromethyl)acetophenone, and 3'-(trifluoromethyl)acetophenone. The composition can include a solvent mixture that includes a fluorinated solvent and a non-fluorinated organic solvent.

Some compositions can include the above-described fluorinated pentacene compound, a fluorinated solvent, an optional non-fluorinated solvent, and another fluorinated liquid such as perfluoroalkanes, perfluorocycloalkanes (e.g. perfluorodecalin), perfluoroheteroalkanes (e.g. perfluorotributylamine, and perfluoropolyethers), perfluoroheterocycloalkanes (e.g. perfluoro(butyltetrahydrofuran)), and fluorinated ethers or polyethers (e.g. 3-ethoxy-1,1,1,2,3,4,4,5,5,6,6,6-dodecafluoro-2-trifluoromethyl-hexane and 2H-perfluoro-5,8,11-trimethyl-3,6,9,12-tetraoxapentadecane). When added these fluorinated liquids often lower the surface tension of the composition and facilitate wetting of various substrate surfaces. These fluorinated liquids may not function as good solvents for the fluorinated pentacene compound.

Typically, one or more of the above-described fluorinated pentacene compounds are present in a given composition at a concentration of at least 0.1 wt % based on a total weight of the composition. The upper limit of the concentration of the fluorinated pentacene compound in the composition is often near the solubility limit of that compound in the particular solvent at the temperature of the composition during its application to a substrate such as in the fabrication of an electronic device. Typical compositions of the present invention comprise one of the above-described fluorinated pentacene compounds at a concentration ranging from about 0.1 wt % to about 5.0 wt %, more typically, from about 0.5 wt % to about 3.0 wt %.

In some embodiments, compositions of the present invention comprise at least one of the above-described fluorinated pentacene compounds and a solvent. In other embodiments, compositions of the present invention comprise at least one of the above-described fluorinated pentacene compounds and a solvent in combination with one or more additional composition components. When present, suitable additional composition components include, but are not limited to, a polymer additive, a rheological modifier, a surfactant, another semiconductor that is a complementary electron transfer partner for the fluorinated pentacene, or a combination thereof. In some exemplary embodiments, the compositions comprise a polymer additive selected from the group consisting of polystyrene, poly(alphamethylstyrene), poly(pentafluorostyrene), poly(methyl methacrylate), poly(4-cyanomethyl styrene), poly(4-vinylphenol), or any other suitable polymer disclosed in U.S. Patent Application Publication No. 2004/0222412 A1 or U.S. Patent Application Publication No. 2007/0146426 A1, the subject matter of both of which is hereby incorporated by reference in its entirety. In some desired embodiments, the polymer additive comprises polystyrene, poly(alpha-methylstyrene), poly(pentafluorostyrene) or poly(methyl methacrylate). In some exemplary embodiments, the compositions comprise a surfactant selected from fluorinated surfactants or fluorosurfactants.

When present, each additional composition component (i.e., components other than the fluorinated pentacene compound) is independently present in an amount of greater than 0 to about 50 wt % based on a total weight of the composition. Typically, each additional composition component (i.e., components other than the fluorinated pentacene compound) is independently present in an amount ranging from about 0.0001 to about 10.0 wt % based on a total weight of the composition. For example, when a polymer additive (e.g., polystyrene) is present in the composition, the polymer additive is typically present in an amount of greater than 0 to about 5.0 wt %, more typically, from about 0.5 to about 3.0 wt % based on a total weight of the composition. For example, when a surfactant is present in the composition, the surfactant is typically present in an amount of greater than 0 to about 1.0 wt %, more typically, from about 0.001 to about 0.5 wt % based on a total weight of the composition.

In some embodiments, the resulting composition desirably has composition properties (e.g., composition stability, viscosity, etc.) that enable the composition to be coated onto a substrate via conventional coating processes. Suitable conventional coating processes include, but are not limited to, spin coating, knife-coating, roll-to-roll web-coating, and dip coating, as well as printing processes such as ink-jet printing, screen printing, and offset lithography. In one desired embodiment, the resulting composition is a printable composition, even more desirably, an ink jet printable composition.

The above-described compositions may be coated onto a substrate. The resulting substrate has at least one coatable surface and a coated layer on the at least one coatable surface, wherein the coated layer comprises a fluorinated pentacene compound having Structure A, wherein R, R', R'', x, y, z and X are as described above. As discussed above, the coated layer may further comprise one or more additional composition components other than at least one of the above-described fluorinated pentacene compounds.

The compositions of the present invention may be coated onto a variety of substrates. Suitable substrates include, but are not limited to, polymeric films such as polyethylene terephthalate (PET), polyethylene naphthalate (PEN), and polyimides, and inorganic substrates such as silica, alumina, silicon wafers, and glass. The surface of a given substrate may be treated, e.g. by reaction of chemical functionality inherent to the surface with chemical reagents such as silanes or exposure of the surface to plasma, in order to alter the surface characteristics. In one exemplary embodiment, the substrate comprises an electronic device or an electronic device component. For example, compositions of the present invention may be coated onto a substrate so as to form a semiconductor layer of an electronic device such as a thin film transistor (TFT), photovoltaic cell, organic light-emitting diode (OLED), or sensor.

Once coated onto a substrate surface, the solvent in the coated layer is removed to form a semiconductor layer. Any suitable method may be used to remove (i.e., dry or evaporate) the solvent in the coated layer. For example, the solvent may be removed by evaporation. Typically, at least about 80 percent of the solvent is removed to form the semiconductor layer. For example, at least about 85 weight percent, at least about 90 weight percent, at least about 92 weight percent, at least about 95 weight percent, at least about 97 weight percent, at least about 98 weight percent, at least about 99 weight percent, or at least about 99.5 weight percent of the solvent is removed.

The solvent often can be evaporated at any suitable temperature. In some methods, the solvent mixture is evaporated at ambient temperature (i.e., at the temperature of the room or facility in which the coating step is carried out). In other methods, the solvent is evaporated at a temperature higher or lower than ambient temperature. For example, a platen supporting the substrate can be heated or cooled to a temperature higher or lower than ambient temperature. In still other methods, some or most of the solvent can evaporate at ambient temperature, and any remaining solvent can be evaporated at a temperature higher than ambient temperature. In methods where the solvent evaporates at a temperature higher than ambient temperature, the evaporation can be carried out under an inert atmosphere, such as a nitrogen atmosphere.

Alternatively, the solvent can be removed by application of reduced pressure (i.e., at a pressure that is less than atmospheric pressure) such as through the use of a vacuum. During application of reduced pressure, the solvent can be removed at any suitable temperature such as those described above.

The rate of removal of the solvent from the coated layer can affect the resulting semiconductor layer. For example, if the removal process is too rapid, poor packing of the semiconductor molecules tend to occur during crystallization. Poor packing of the semiconductor molecules can be detrimental to the electrical performance of the semiconductor layer. The solvent can evaporate entirely on its own in an uncontrolled fashion (i.e., no time constraints), or the conditions can be controlled in order to control the rate of evaporation. In order to minimize poor packing, the solvent can be evaporated while slowing the evaporation rate by covering the coated layer. Such conditions can lead to a semiconductive layer having a relatively high crystallinity.

After removal of a desired amount of solvent to form the semiconductor layer, the semiconductor layer can be annealed by exposure to heat or solvent vapors, i.e., by thermal annealing or solvent annealing.

Exemplary electronic devices of the present invention may be fabricated by deposition of the above-described fluorinated pentacenes onto a substrate. Deposition of the fluorinated pentacenes can be accomplished by any means, such as by vapor phase deposition (for example, vacuum deposition), application or coating of the pentacene in the melt, or by solution coating and printing processes.

Exemplary electronic devices of the present invention may have a top contact/bottom gate TFT construction as shown in FIG. 1. As shown in FIG. 1, exemplary electronic device 10 comprises substrate 11, gate electrode 16, dielectric layer 12, semiconductor layer 13, source electrode 14, and drain electrode 15. Materials for forming substrate 11, gate electrode 16, dielectric layer 12, source electrode 14, and drain electrode 15 of exemplary electronic device 10 may comprise any materials typically used to form TFT electronic devices.

Suitable materials for forming substrate 11 include, but are not limited to, glass, polyethylene terephthalate, polyethylene naphthalate, and polyimide. Suitable materials for forming dielectric layer 12 include, but are not limited to, any of a variety of polymers such as poly(4-vinylphenol), poly(methylmethacrylate), and poly(4-cyanomethylstyrene), which are typically deposited from solution, but may also be formed in place via curing of a formulation containing functional monomers and/or oligomers and a curing agent. The dielectric layer 12 may further include inorganic fillers such as, but not limited to, $BaTiO_3$, $SiO_2$, $ZrO_2$, which act to enhance the dielectric constant of dielectric layer 12.

Suitable materials for forming semiconductor layer 13 comprise the above-described compositions of the present invention. Suitable materials for forming each of gate electrode 16, source electrode 14 and drain electrode 15 include, but are not limited to, carbon nanotubes, poly(3,4-ethylenedioxythiophene) (PEDOT) doped with sulfonated polystyrene, polyaniline (PANI), gold, silver, aluminum, copper, titanium, palladium, platinum, chromium, as well as blends thereof (e.g., blends, alloys, multi-layer composites of the various electrode materials).

In some cases, the substrate 11, the gate electrode 16, and the dielectric layer 12 are heavily-doped n-type silicon wafers with thermal oxide (such as those commercially available from Noel Technologies, Inc. (Campbell, Calif.)), wherein the heavily-doped n-type silicon wafer serves as both the substrate and gate electrode, and the thermal oxide serves as the dielectric layer.

In some exemplary embodiments, one or more of the following layers are printable (e.g., ink jet printable) layers: gate electrode 16, dielectric layer 12, semiconductor layer 13, source electrode 14, and drain electrode 15. For example, suitable printable compositions for forming dielectric layer 12, gate electrode 16, source electrode 14, and drain electrode 15 are disclosed in U.S. Patent Application Publication No. 20070114516 A1, now U.S. Pat. No. 7,498,662, the subject of which is incorporated herein by reference in its entirety.

Figure 2:
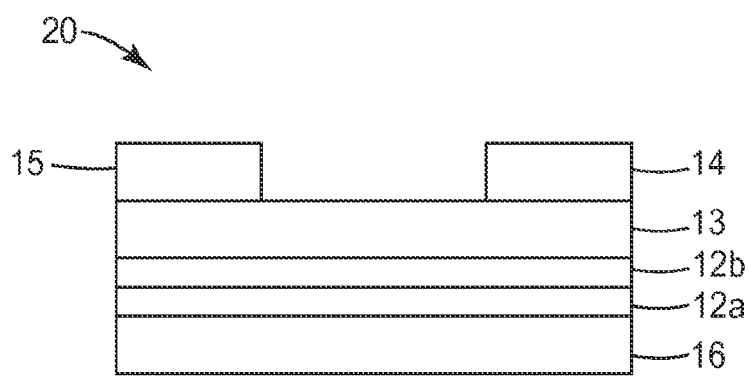
FIG. 2 is a cross-sectional view of another exemplary thin film transistor comprising a semiconductor layer formed via solution deposition of a composition containing at least one fluorinated pentacene compound of the present invention.

Electronic devices of the present invention desirably comprise at least one of the above-mentioned fluorinated pentacene compounds. Such electronic devices may comprise, for example, the following specific top contact/bottom gate TFT construction as shown in exemplary device 20 of FIG. 2: a gate electrode layer 16 comprising a heavily n-doped silicon wafer with a first dielectric layer 12a in the form of a thermal oxide ($SiO_2$) layer positioned over the gate electrode layer 16 (e.g., a heavily n-doped silicon wafer commercially available from Noel Technologies, Inc. (Campbell, Calif.)); a second dielectric layer 12b comprising a polymeric dielectric composition comprising SARTOMER™ SR-368 (Sartomer Company Inc. (Exton, Pa.)) (about 8.5 wt %), zirconia nanoparticles surface treated with gamma-methacryloxypropyltrimethoxysilane (SILQUEST® A-174 silane from OSi Specialties (South Charleston, W. Va.)) and formed as disclosed in U.S. patent application Ser. Nos. 11/771,787, now published as U.S. Patent Publication No. 2009/0004771), and 11/771,859, now published as U.S. Patent Publication No. 2009/0001356) (see, for example, "Preparatory Example 1—Dielectric Ink" in each application), the subject matter of which is hereby incorporated by reference in its entirety (about 40.0 wt %), IRGACURE™ 184 photoinitiator (Ciba Corporation (Newport, Del.)) (about 1.5 wt %), and isophorone (Sigma-Aldrich (Milwaukee, Wis.)) (about 50.0 wt %); a semiconductor layer 13 formed from a composition comprising at least one of the above-described fluorinated pentacene compounds (about 2.0 wt %), polystyrene (Polymer Source Inc. (Montreal, Canada)) (about 1.0 wt %), and butylbenzene (Sigma-Aldrich (Milwaukee, Wis.)) (about 97.0 wt %); a source electrode 14 comprising gold; and a drain electrode 15 comprising gold.

Figure 3:
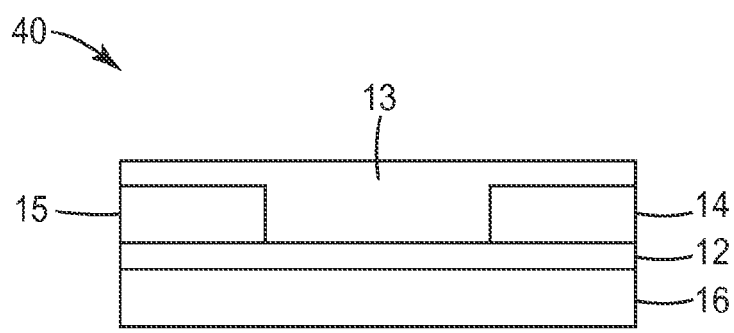
FIG. 3 is a cross-sectional view of yet another exemplary thin film transistor comprising a semiconductor layer formed via solution deposition of a composition containing at least one fluorinated pentacene compound of the present invention.

Other exemplary electronic devices of the present invention may have a construction as shown in FIG. 3. As shown in FIG. 3, exemplary electronic device 30 comprises gate electrode 16, dielectric layer 12, source electrode 14, drain electrode 15, and semiconductor layer 13 comprising at least one fluorinated pentacene compound of the present invention.

It is believed that the addition of at least one of the above-described fluorinated pentacene compounds into a composition or into an electronic device of the present invention provides one or more advantages:

(1) more deposition and crystallization of a semiconductor laterally along a surface (i.e., in the x-y plane) rather than up off of the surface or out of the x-y plane of the surface (i.e., in the z direction) relative to similar semiconductor layers without one of the fluorinated pentacene compounds of the present invention;

(2) results in a morphology where the semiconductor resides at the interface between (i) the surface and a polymer or (ii) at the air and polymer interface (In the former, if the surface is a gate dielectric, the morphology is preferable for a bottom gate TFT. In the latter, the morphology is advantageous to the construction of a top gate TFT by subsequent deposition of a gate dielectric on top of the organic semiconductor);

(3) improves the ability of a solution to wet a surface beyond that obtained with a similar semiconductor without one of the fluorinated pentacene compounds of the present invention;

(4) increased solubility or dispersibility in fluorinated solvents, that have very low surface tensions alone or in conjunction with fluorosurfactants or other fluorinated liquids, and thus provide superior wetting of surfaces, such as low energy surfaces including hydrocarbon and fluorocarbon surfaces;

(5) increased hydrophobicity and/or oleophobicity, thus protecting the electronic device from moisture and organic solvents;

(6) reduced susceptibility of the composition or electronic device to oxidation; and (7) increased photochemical stability of the composition or electronic device.

The above-described fluorinated pentacene compounds of the present invention may be prepared by a method comprising the steps of forming a substituted silyl acetylene having a desired combination of R, R' and R" substituents, and then reacting the substituted silyl acetylene with 6,13-pentacenequinone. The step of forming a substituted silyl acetylene having a desired combination of R, R' and R" substituents may comprise a number of process steps including, but not limited to, a first substitution reaction wherein a trimethylsilyl acetylene group substitutes a labile group (typically a halogen) on a disubstituted chloro silane (e.g., chloro diisopropylsilane), followed by conversion of the silanyl hydrogen to a halogen by any of a number of known transformations (e.g., treatment with N-bromosuccinimide in a solvent such as dichloromethane), followed by substitution of this newly generated labile group by a third substituent (e.g., a fluorinated monovalent radical). Alternatively, one labile group of a fluoroalkyltrichlorosilane can be displaced by an alkyne (e.g. a trimethylsilyl-substituted acetylene), and the remaining halogens subsequently replaced with other substituents (e.g., isopropyl groups). The desired terminal acetylene is then generated by selective removal of the trimethylsilyl group under mild basic conditions. A third alternative involves the substitution of the chloride substituent of commercially available fluoroalkyl dialkyl silyl chlorides with a terminal acetylide, yielding the desired acetylene directly. A fourth alternative involves the conversion of the silanyl hydrogen of commercially available fluoroalkyl dialkyl silanes to a halogen, for example, by a hydrogenbromine exchange reaction using a transition metal catalyst in the presence of allyl bromide or an alkyl bromide, followed by substitution of this newly generated labile group (halogen) by acetylene or trimethylsilylacetylene. In the case of the latter, the desired terminal acetylene is then generated by selective removal of the trimethylsilyl group under mild basic conditions. The methods of forming fluorinated pentacene compounds of the present invention may further comprise one or more of the following method steps: purification by at least one, and in some cases, two or three recrystallization steps from a suitable solvent such as acetone, wherein the fluorinated pentacene compound is dissolved in an amount of boiling acetone, which dissolves all solids and is then cooled to about 0-4° C. while protecting the solution from light to prevent photodegradation. The solids are then collected by filtration and dried in vacuum to remove residual acetone.

Once formed, fluorinated pentacene compounds of the present invention may be combined with a solvent and one or more additional components to form compositions, such as printable compositions. As discussed above, fluorinated pentacene compounds of the present invention may be incorporated into at least one of the above-referenced organic solvents (e.g., 3-(trifluoromethyl)anisole) to form a first composition. Additional composition components such as those described above (e.g., polystyrene) may be incorporated into the first composition to provide a final composition. Desirably, the final composition is printable via an ink jet printing apparatus.

The compositions of the present invention containing at least one of the above-described fluorinated pentacene compounds of the present invention may be used to form a variety of coatings, substrates having a coated layer thereon, electronic device components, and electronic devices. Desirably, the resulting coating, substrate having a coated layer thereon, electronic device component, or electronic device comprises a fluorinated pentacene compound having Structure A, wherein R, R', R", x, y, z and X are as described above. More desirably, the resulting coating, substrate having a coated layer thereon, electronic device component, or electronic device comprises a fluorinated pentacene compound having Structure A, wherein z=0, R and R' together comprise two identical groups (e.g., two alkyl groups, two cycloalkyl groups, or two alkenyl groups) and one dissimilar group (e.g., a fluorinated monovalent radical comprising one or more fluorine atoms with the one or more fluorine atoms being separated from silicon atom by at least three atoms or four covalent bonds). In some desired embodiments, the resulting coating, substrate having a coated layer thereon, electronic device component, or electronic device comprises a fluorinated pentacene compound having Structure A, wherein z=0, R comprise methyl, isopropyl, isopropenyl, or cycloalkyl (e.g., cyclopropyl, cyclobutyl, or cyclopentyl), and R' comprises any one of the above-described fluorinated monovalent radicals.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

These examples are merely for illustrative purposes only and are not meant to be limiting on the scope of the appended claims. All parts, percentages, ratios, etc. in the examples and the rest of the specification are by weight unless indicated otherwise. The materials used in the examples were obtained from the sources indicated in Table 3 unless specifically indicated otherwise in an individual example.

TABLE 3

Materials Used in Examples

| Material | Abbreviation (if any) | Source |
|---|---|---|
| Acetic acid (99.7+%, A.C.S. reagent) | | Sigma-Aldrich (Milwaukee, WI) |
| Allyl bromide | | |
| Anisole | | |
| 2,2'-Azobis(2-methylpropionitrile) | AIBN | |
| Benzene | | |
| N-Bromosuccinimide | | |
| N-butylbenzene | | |
| N-butyllithium | n-BuLi | |
| Chlorobenzene | | |
| Chloroform (ReagentPlus, ≥99.8%, contains 0.5-1.0% ethanol as stabilizer) | | |
| Copper (I) iodide | | |
| Cyclohexane-1,4-dione | | |
| Decane | | |
| Dichloroethane (≥99%, A.C.S. reagent) | | |
| Diisobutylaluminum hydride | | |
| Dimethylacetylene dicarboxylate | | |
| 2,3-Dimethyl-1,3-butadiene | | |
| Dimethylformamide (>99.8%) | | |
| 1,2-dimethyl-4-pentafluoroethylbenzene | | |
| 4,5-Dimethyl phthalaldehyde | | |
| Ethanol (absolute, >99.5%) | | |
| Ethyl acetate (A.C.S. reagent, 99.5+%) | | |
| Ethylbenzene | | |
| Ethynylmagnesium bromide | | |
| Heptane (ReagentPlus, 99%) | | |
| Hydrobromic acid (A.C.S. reagent, 48%) | | |
| Hydrochloric acid (A.C.S. reagent, 37%) | | |
| Isopropenylmagnesium bromide | | |
| Isopropylmagnesium chloride | | |
| Isopropyllithium | | Sigma-Aldrich (Milwaukee, WI) |
| Isophorone | | |
| N-methylpyrrolidinone (anhydrous) | | |
| Palladium chloride | PdCl$_2$ | |
| 6,13-Pentacenequinone | | |
| 2-Pentafluoroethylpentacene-6,13-dione | | |
| Phthalaldehyde | | |
| Sodium methoxide in methanol | | |
| Sodium pentafluoropropionic acid | | |
| Stannous chloride dihydrate | | |
| Sulfuric acid (95-98%) | | |
| Tetrahydrofuran (anhydrous) (>99.9% inhibitor-free) | THF | |
| Tetrahydrofuran (A.C.S. reagent >99.0%) | THF | |
| Toluene (anhydrous, 99.8%) | | |
| Trimethylsilyl acetylene | | GFS Chemical (Columbus, OH) |
| n-doped silicon wafers with thermal oxide (heavily doped) | | Noel Technologies, Inc. (Campbell, CA) |
| Polystyrene (118K MW) | | Polymer Source Inc. (Montreal, Canada) |
| SARTOMER ™ SR-351 | | Sartomer Company Inc. (Exton, PA) |
| SARTOMER ™ SR-368 | | |
| Ink jet printable silver ink Cabot AG-IJ-G-100-S1 | | Cabot Corporation (Alburquerque, NM) |

TABLE 3-continued

Materials Used in Examples

| Material | Abbreviation (if any) | Source |
|---|---|---|
| IRGACURE ™ 184 photoinitiator | | Ciba Corporation (Newport, DE) |
| N-methylnonafluorobutane-sulfonamide | | 3M Company (St. Paul, MN) |
| Platinum(0)-1,3-divinyl-1,1,3,3-tetramethyldisiloxane complex (18% in toluene) | | |
| zirconia nanoparticles surface treated with silane A-174[1] | | |
| Diisopropylchlorosilane | | Gelest (Morrisville, PA) |
| 3,3,3-trifluoropropyltrichlorosilane | | |
| 3,3,4,4,5,5,6,6-nonafluoro-hexyldimethylchlorosilane | | |
| 3,3,4,4,5,5,6,6,6-nonafluorohexyltrichlorosilane | | |
| 3,3,4,4,5,5,6,6,7,7,8,8,8-tridecafluorooctyldimethylchlorosilane | | |
| 3,3,4,4,5,5,6,6,7,7,8,8,9,9,10,10,10-heptadecafluorodecyltrichlorosilane | | Gelest (Morrisville, PA) |
| (3-heptafluoroisopropoxy)-propyltrichlorosilane | | |
| 3,3,4,4,5,5,6,6,7,7,8,8,9,9,10,10,10-heptadecafluorodecyldiisopropyl-silane | | Fluorous Technologies Inc. (Pittsburgh, PA) |
| (3,3,4,4,5,5,6,6,7,7,8,8,9,10,10,10-hexadecafluoro-9-trifluoromethyldecyl)diisopropyl-silane | | |
| (3,3,4,4,5,5,5-heptafluoropentyl)diisopropyl-silane | | |
| 3,3,4,4,5,5,6,6,6-nonafluoro-hexyldiisopropylsilane | | |
| 3,3,4,4,5,5,6,6,7,7,8,8,8-tridecafluorooctyldiisopropylsilane | | |
| 1,4-Anthraquinone | | Alfa Aesar (Ward Hill, MA) |
| 3-Fluoro-o-xylene | | |
| 4-Iodo-o-xylene | | |
| 3-(trifluoromethyl)anisole | | |
| Potassium iodide | | EMD Chemicals Inc. (Gibbstown, NJ) |
| toluene (Omnisolv ™ High Purity) | | |
| 4-Trifluoromethyl-1,2-phthalic acid | | TCI America (Portland, OR) |
| Acetone | | Pharmco-Aaper |
| Dichloromethane | DCM | (Shelbyville, KY) |
| Diethyl ether | | |
| Hexane | | |
| Methanol | | |
| n-Pentane | | |
| Ammonium chloride, crystal | | Mallinckrodt Baker Inc. |
| Magnesium sulfate | MgSO$_4$ | (Phillipsburg, NJ) |
| Sodium hydroxide, pellet | | |

[1]The method of forming zirconia nanoparticles surface treated with silane A-174 as used in the present invention is disclosed in U.S. patent applications Nos. 11/771,787 and 11/771,859, now U.S. patent application Publication Nos. US2009/0004771 and US2009/0001356 respectively (see, for example, "Preparatory Example 1 - Dielectric Ink" in each application), both of which were filed on and assigned to The 3M Company (St. Paul, MN), the subject matter of both of which is incorporated herein by reference in its entirety.

Test Methods:
Mobility Value Test Method I:

The saturation field effect mobility (μ) was determined in air using two Source Measure Units (Model 2400 from Keithley Instruments, Inc. (Cleveland, Ohio)). The devices were placed on an S-1160 Series probe station and probes connected using S-725-PRM manipulators (both available from Signatone Corp. (Gilroy, Calif.)). The drain to source bias voltage ($V_{DS}$) was held at −40 V, while the gate to source bias ($V_{GS}$) was incremented over the range +10 V to −40 V in 1 V steps. The drain-source current ($I_{DS}$) was measured as a function of gate-source voltage bias ($V_{GS}$) from +10V to −40V at a constant drain-source voltage bias ($V_{DS}$) of −40V. The saturation field effect mobility (μ) was calculated from the slope of the linear portion of the plot of the square root of $I_{DS}$ versus $V_{GS}$ using the equation:

$$I_{DS} = \mu WC(V_{GS} - V_t)^2 \div 2L$$

wherein C is the specific capacitance of the gate dielectric, W is the channel width, and L is the channel length.

Using a plot of the square root of $I_{DS}$ versus $V_{GS}$ curve, the X-axis extrapolation of a straight-line fit was taken as the threshold voltage ($V_t$). In addition, plotting $I_{DS}$ (using a log-scale) as a function of $V_{GS}$ afforded a curve where a straight line fit was drawn along a portion of the curve containing $V_t$. The inverse of the slope of this line was the sub-threshold slope (S). The on/off ratio was taken as the difference between the minimum and maximum drain current ($I_{DS}$) values of the $I_{DS}$–$V_{GS}$ curve.

Mobility Value Test Method II:

The average mobility of each sample was determined in air under ambient lighting using two Source Measure Units (Model 2400 from Keithley Instruments, Inc. (Cleveland, Ohio)). The devices were placed on an S-1160 Series probe station and probes connected using S-725-PRM manipulators (both available from Signatone Corp. (Gilroy, Calif.)). The drain to source bias voltage ($V_{DS}$) was held at −40 V, while the gate to source bias ($V_{GS}$) was incremented over the range +10 V to −40 V in 1 V steps. The average mobility value was calculated from the measurement of 10 transistors on each substrate.

The "effective channel width" of each device was determined because dip coating did not always result in complete coverage of the substrate. The percentage of substrate surface covered by dried semiconductor composition was measured by (i) taking three digital photos of the substrate at high magnification (100×), then (ii) using photo editing software (available under the trade designation PHOTOSHOP CS3 from Adobe Systems Inc. (San Jose, Calif.)) to identify and render areas of exposed substrate as uniform black (0,0,0) coloration in L,a,b color space, then (iii) using the histogram feature of the photo editing software to identify the percentage of photo with luminosity (L)<15, and then (iv) averaging the result of the three photos to give a value for surface coverage of the substrate. The value of surface coverage was then used to calculate the effective channel width of the TFTs, and this effective channel width was used to calculate charge carrier mobility values. The following formula was used to calculate effective channel width:

$$W_{eff} = \left(\frac{W_{dep}}{100}\right) * Cov$$

wherein $W_{eff}$ is the effective channel width, $W_{dep}$ is the length of source and drain contacts (as-deposited), and $C_{ov}$ is the surface coverage (in percent). For example, if the source and drain electrodes were 1000 microns long and the surface coverage was 80 percent, then the effective channel width would be 800 microns.

Figure 4:
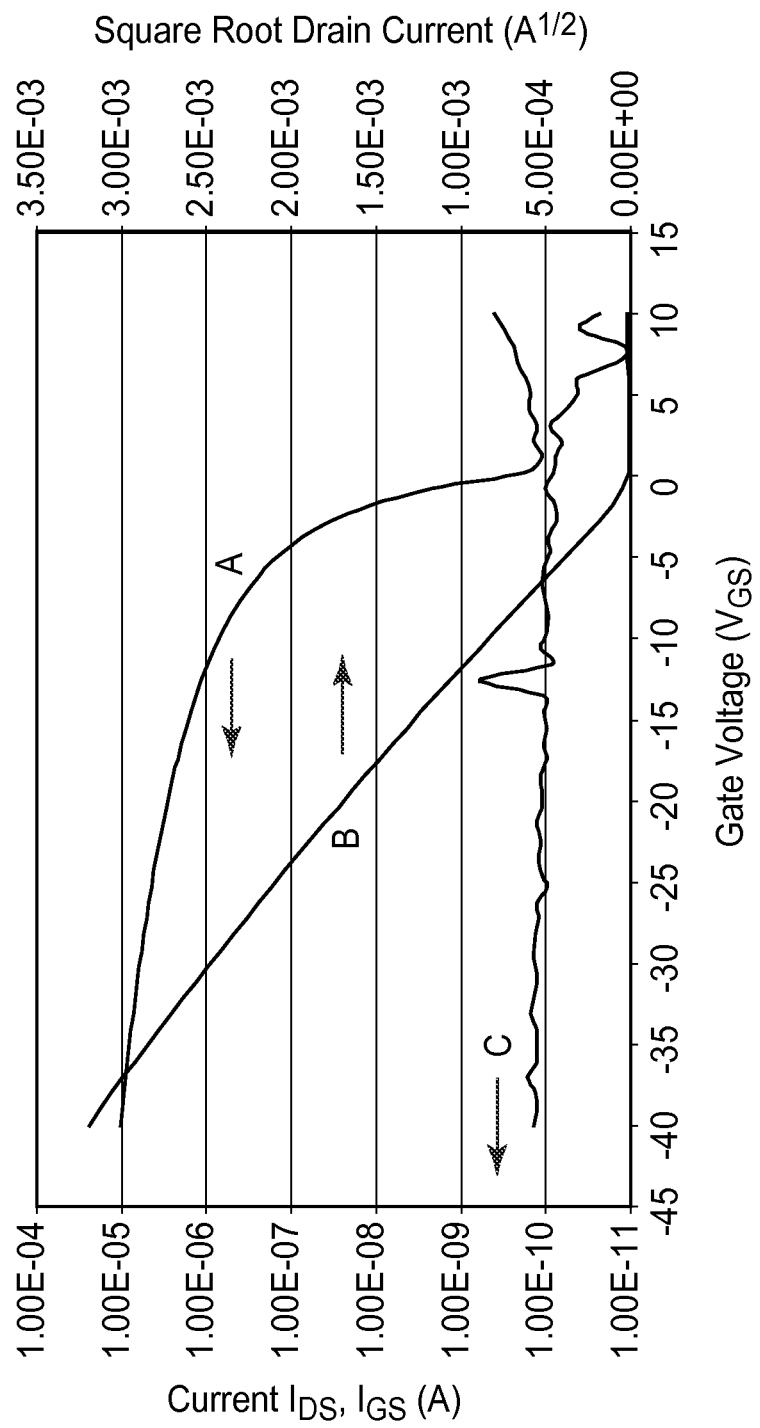
FIG. 4 is a representative plot of transistor outputs ($I_{DS}$ and $(I_{DS})^{1/2}$) as a function of sweeping gate bias.

FIG. 4 graphically displays exemplary measured parameters. In FIG. 4, traces labeled "A" indicate measured drain current ($I_{DS}$) as a function of $V_{GS}$. Traces labeled "B" indicate the square root of measured drain current ($I_{DS}$) versus $V_{GS}$, and traces labeled "C" indicate measured gate current ($I_{GS}$) versus $V_{GS}$. The saturated field effect mobility (μ) was calculated from the slope (m) of the plot of the square root of drain current versus $V_{GS}$ (trace "B") using the following equation:

$$\mu = 2\left(\frac{m^2 L}{WC}\right)$$

wherein C is the specific capacitance of the gate dielectric, W is the effective channel width, and L is the channel length. The mobility value for each sample was the maximum mobility value observed over the range of measurement.

Example 1

Synthesis of 6,13-Bis(3,3,3-trifluoropropyldiisopropylsilylethynyl)pentacene

Synthesis of (3,3,3-trifluoropropyldiisopropylsilyl)acetylene

In an oven-dried 250-mL round bottom flask, 4.12 g (42.0 mmol) of trimethylsilylacetylene was dissolved in 45 mL of anhydrous THF. The solution was cooled to 0° C., then n-butyllithium (14.8 mL, 37 mmol, 2.5 M in hexane) was added dropwise. Stirring was continued for 1 hr and the colorless solution was allowed to warm to room temperature. In a second oven-dried 500-mL round bottom flask, 3,3,3-trifluoropropyltrichlorosilane (8.1 g, 35 mmol) was dissolved in anhydrous THF (35 mL). The first reaction mixture was added to the second solution dropwise over 1 hr, followed by stirring for 5 hrs. The new reaction mixture was cooled to 0° C., then isopropyllithium (123 mL, 86 mmol, 0.7 M in pentane) was added dropwise, and the solution was allowed to warm to room temperature over 12 hrs. The entire mixture was poured into 150 mL of a dilute solution of ammonium chloride, and hexane (100 mL) was added. The organic layer was separated, and the aqueous layer was extracted a second time with hexane (20 mL). The organic layers were combined, washed with water (3×20 mL), dried over magnesium sulfate, filtered, and concentrated under vacuum. The trimethylsilyl-capped product was purified by column chromatography on silica gel using hexane as an eluant ($R_f$~0.6 in hexane), yielding 7.7 g of a colorless liquid. The trimethylsilyl group was removed by dissolving the product in THF (20 mL) and adding methanol (20 mL) and 3 drops of a 15% sodium hydroxide solution, followed by stirring for 30 minutes. The crude product was isolated, then flushed through a thin pad of silica using hexane and concentrated under vacuum to yield 4.9 g (21 mmol, 60% from the starting silane) of a colorless liquid. Analysis of the colorless product provided the following data: $^1$H-NMR (200 MHz, CDCl$_3$) δ=2.4 (s, 1H), 2.2 (m, 2H), 1.1 (m, 14H), 0.8 (m, 2H).

Synthesis of 6,13-Bis(3,3,3-trifluoropropyldiisopropylsilylethynyl)pentacene (3,3,3-trifluoropropyldiisopropylsilyl)acetylene (1.3 g, 5.7 mmol) and anhydrous THF were added to an oven-dried 100-mL round bottom flask equipped with a stir bar. Isopropylmagnesium chloride (2 mL, 2 M in THF) was added dropwise, and the solution was heated to 60° C. for 1 hr. The mixture was removed from the heat and pentacene quinone (0.47 g, 1.5 mmol) was added. Heating at 60° C. was resumed and continued for 12 hr. The homogeneous reaction mixture was cooled to room temperature, then quenched by the addition of 0.5 mL of a saturated solution of ammonium chloride. Stannous chloride dihydrate (1.2 g, 5.3 mmol) was dissolved in 3 mL of 10% hydrochloric acid solution, then added to the quenched reaction mixture, and stirring was continued for 15 minutes. Hexane (50 mL) and water (20 mL) were added and the organic layer was separated. The organic layer was washed repeatedly and alternately with 10% hydrochloric acid solution and water, then dried over magnesium sulfate, and rinsed onto a thick pad of silica gel and flushed with additional hexane (200 mL). The product was eluted using 9:1 hexane:dichloromethane. Removal of solvent yielded 0.50 g (0.67 mmol, 45% relative to quinone) of blue powder, which was recrystallized from acetone to yield 0.44 g of blue needles. Analysis of the product provided the following data: $^1$H-NMR (200 MHz, CDCl$_3$) δ=9.2 (s, 4H), 8.0 (dd, J=3.3 Hz, 6.6 Hz, 4H), 7.4 (dd, J=3.3 Hz, 6.6 Hz, 4H), 2.5 (m, 4H), 1.4 (m, 28H), 1.2 (m, 4H).

Example 2

Synthesis of 6,13-Bis(3,3,4,4,5,5,6,6,6-nonafluoro-hexyldimethylsilylethynyl)pentacene Synthesis of (3,3,4,4,5,5,6,6,6-nonafluorohexyldimethylsilyl)acetylene In an oven-dried 250-mL round bottom flask, 3,3,4,4,5,5,6,6,6-nonafluorohexyldimethylchlorosilane (4.58 g, 13.4 mmol) was dissolved in anhydrous THF (10 mL) and cooled in an ice bath. Ethynylmagnesium bromide (34 mL, 17 mmol, 0.5 M in THF) was added slowly, then the mixture was heated to 60° C. for 12 hr. The reaction was quenched with water and dilute sulfuric acid (i.e., a 10 wt % solution of the sulfuric acid (95-98%) in water) to dissolve the salts, then hexane was added and the organic layer was separated. The organic layer was washed with water (5×20 mL), dried over magnesium sulfate, filtered, and concentrated under vacuum to yield the crude product. Purification using chromatography on silica gel with hexane as an eluant yielded a colorless liquid (3.52 g, 10.6 mmol, 80%). Analysis of the colorless product provided the following data: $^1$H-NMR (200 MHz, CDCl$_3$) δ=2.4 (s, 1H), 2.1 (m, 2H), 0.8 (m, 2H), 0.2 (s, 6H).

Synthesis of 6,13-Bis(3,3,4,4,5,5,6,6,6-nonafluoro-hexyldimethylsilylethynyl)-pentacene In an oven-dried 100-mL round bottom flask, (3,3,4,4,5,5,6,6,6-nonafluorohexyldimethylsilyl)acetylene (1.25 g, 3.78 mmol) was dissolved in anhydrous THF (5 mL). Isopropylmagnesium chloride (1.1 mL, 2.2 mmol, 2 M in THF) was added, and the solution was heated to 60° C. for 2 hr. The reaction mixture was removed from the heat and pentacene quinone (0.25 g, 0.80 mmol) was added, followed by heating to 60° C. for 12 hr. The reaction was quenched by the addition of 4 drops of saturated ammonium chloride solution, then stannous chloride dihydrate (0.63 g, 2.8 mmol) dissolved in 1 mL 10% hydrochloric acid solution was added and stirring was continued for 5 minutes. The product was precipitated by the addition of water (10 mL), and collected by filtration, then dissolved in hexane and dried over magnesium sulfate. The hexane solution was rinsed onto a thick pad of silica gel, and flushed with additional hexane to elute the excess acetylene, then the product was eluted using 9:1 hexane:dichloromethane. Removal of solvent yielded 0.4 g of a blue solid, which was recrystallized from acetone (~12 mL) to yield 0.23 g (0.25 mmol, 31%) of blue needles. Analysis of the product provided the following data: $^1$H-NMR (200 MHz, CDCl$_3$) δ=9.1 (s, 4H), 8.0 (dd, J=3.2 Hz, 6.6 Hz, 4H), 7.6 (dd, J=3.0 Hz, 6.6 Hz, 4H), 2.4 (m, 4H), 1.2 (m, 4H), 0.6 (s, 12H).

Example 3

Synthesis of 6,13-Bis(3,3,4,4,5,5,6,6,6-nonafluoro-hexyldiisopropylsilylethynyl)pentacene Synthesis of (3,3,4,4,5,5,6,6,6-nonafluorohexyldiisopropylsilyl)acetylene To an oven-dried 250-mL round bottom flask was added 3,3,4,4,5,5,6,6,6-nonafluorohexyltrichlorosilane (4.52 g, 11.9 mmol) and anhydrous THF (20 mL). Isopropyllithium (34 mL, 24 mmol, 0.7 M in pentane) was added dropwise over 1 hr, then stirring was continued for 4 hr. Ethynylmagnesium bromide (32 mL, 16 mmol, 0.5 M in THF) was added slowly, then the reaction mixture was heated to 50° C. for 12 hr. The reaction was quenched with water and dilute sulfuric acid to dissolve the salts, then hexane was added and the organic layer was separated. The organic layer was washed with water (5×20 mL), dried over magnesium sulfate, filtered, and concentrated under vacuum to yield the crude product mixture. Purification by silica chromatography with hexane as an eluant (R$_f$~0.6 in hexane) yielded 1.8 g (4.6 mmol, 31%) of the desired product as a colorless liquid. Analysis of the colorless product provided the following data: $^1$H-NMR (200 MHz, CDCl$_3$) δ=2.4 (s, 1H), 2.2 (m, 2H), 1.1 (m, 14H), 0.8 (m, 2H).

Synthesis of 6,13-Bis(3,3,4,4,5,5,6,6,6-nonafluoro-hexyldiisopropylsilylethynyl)-pentacene In an oven-dried 100-mL round bottom flask, (3,3,4,4,5,5,6,6,6-nonafluorohexyldiisopropylsilyl)acetylene (1.7 g, 4.5 mmol) was dissolved in anhydrous THF (5 mL), then cooled in an ice bath. n-Butyllithium (1.4 mL, 3.6 mmol, 2.5 M in hexane) was added dropwise, then stirring was continued for 30 min. Pentacene quinone (0.44 g, 1.4 mmol) was added and the reaction mixture was stirred for 12 hr. The reaction was quenched by the addition of 4 drops of a saturated ammonium chloride solution, then stannous chloride dihydrate (1.1 g, 5.0 mmol) dissolved in 1 mL of a 10% hydrochloric acid solution was added and this solution was stirred for 5 minutes. Hexane was added, and the organic layer was separated, dried over magnesium sulfate, and concentrated under vacuum. The crude product was taken up in hexane and rinsed onto a thick pad of silica followed by flushing with hexane to elute the excess acetylene. The product was eluted using 9:1 hexane:dichloromethane. Concentration under vacuum yielded a thick blue oil, which was recrystallized from acetone (~2 mL) (5 days at room temperature) to yield 30 mg (0.03 mmol, 2%) of burgundy elongated plates. Analysis of the product provided the following data: $^1$H-NMR (200 MHz, CDCl$_3$) δ=9.2 (s, 4H), 8.0 (dd, J=3.0 Hz, 6.6 Hz, 4H), 7.4 (dd, J=3.2 Hz, 7.0 Hz, 4H), 2.5 (m, 4H), 1.3 (m, 28H), 0.8 (m, 4H).

Example 4

Synthesis of 6,13-Bis(3,3,4,4,5,5,6,6,7,7,8,8,8-tridecafluorooctyldimethylsilylethynyl)pentacene Synthesis of (3,3,4,4,5,5,6,6,7,7,8,8,8-tridecafluorooctyldimethylsilyl)acetylene In an oven-dried 250-mL round bottom flask, 3,3,4,4,5,5,6,6,7,7,8,8,8-tridecafluorooctyldimethylchlorosilane (9.67 g, 21.9 mmol) was dissolved in 20 mL anhydrous THF. Ethynylmagnesium bromide (50 mL, 25 mmol, 0.5 M in THF) was added and the mixture was heated to 60° C. for 12 hr. After allowing the mixture to cool to room temperature, the reaction was quenched by the dropwise addition of water, followed by the addition of dilute sulfuric acid to dissolve the magnesium salts. The organic layer was separated, washed with water (3×20 mL) and brine, dried over magnesium sulfate, filtered and concentrated under vacuum. The crude product was purified by chromatography on silica gel using hexane as an eluant. Removal of solvent yielded 9.0 g (21 mmol, 96%) of the product as a colorless liquid. Analysis of the colorless product provided the following data: $^1$H-NMR (200 MHz, CDCl$_3$) δ=2.4 (s, 1H), 2.1 (m, 2H), 0.8 (m, 2H), 0.2 (s, 6H).

Synthesis of 6,13-Bis(3,3,4,4,5,5,6,6,7,7,8,8,8-tridecafluorooctyldimethylsilylethynyl)pentacene Using a First Method In an oven-dried 100-mL round bottom flask, (3,3,4,4,5,5,6,6,7,7,8,8,8-tridecafluorooctyldimethylsilyl)acetylene (2.3 g, 5.3 mmol) was dissolved in 8 mL anhydrous THF. Isopropylmagnesium chloride (2.4 mL, 2 M in THF) was added dropwise, and the solution was heated to 60° C. for 2 hrs. The mixture was removed from the heat and pentacene quinone (0.63 g, 2.0 mmol) was added. Heating at 60° C. was resumed and continued for 12 hr. The homogeneous reaction mixture was cooled to room temperature, then quenched by the addition of 0.5 mL of a saturated solution of ammonium chloride. In a separate Erlenmeyer flask with a stir bar, stannous chloride dihydrate (7.0 mmol, 1.6 g) was dissolved in methanol (150 mL), then 2 mL 10% hydrochloric acid were added. After cooling the methanol solution for 1 hr, the reaction mixture was diluted with methanol (50 mL), then rinsed into the Erlenmeyer flask with additional MeOH (20 mL) and allowed to stir for 15 minutes at room temperature. This mixture was cooled for 1 hr, then the solid was collected by filtration, rinsed with methanol, and dried in ambient atmosphere. This solid was taken up in minimal dichloromethane, diluted with hexane (about 9:1 hexane:dichloromethane), then rinsed onto a medium pad of silica gel and eluted with 9:1 hexane:dichloromethane. Removal of solvent yielded 0.61 g of a shiny blue solid, that was recrystallized from acetone (~160 mL) to yield 0.48 g blue needles (0.42 mmol, 21% from the quinone). Analysis of the product provided the following data: $^1$H-NMR (200 MHz, CDCl$_3$) δ=9.1 (s, 4H), 8.0 (dd, J=3.3 Hz, 6.6 Hz, 4H), 7.4 (dd, J=3.3 Hz, 6.6 Hz, 4H), 2.4 (m, 4H), 1.2 (m, 4H), 0.6 (s, 12H).

Example 5

Synthesis of 6,13-Bis(3,3,4,4,5,5,6,6,7,7,8,8,9,9,10,10,10-heptadecafluorodecyldiisopropylsilylethynyl)pentacene Synthesis of (3,3,4,4,5,5,6,6,7,7,8,8,9,9,10,10,10-heptadecafluorodecyldiisopropylsilyl)acetylene In an oven-dried 250-mL round bottom flask, 3,3,4,4,5,5,6,6,7,7,8,8,9,9,10,10,10-heptadecafluorodecyltrichlorosilane (8.7 g, 15 mmol) was dissolved in anhydrous THF (10 mL). In a separate oven-dried 100-mL round bottom flask, (trimethylsilyl)acetylene (1.7 g, 18 mmol) was dissolved in anhydrous THF (15 mL) and cooled in an ice bath, followed by the dropwise addition of n-butyllithium (6.0 mL, 15 mmol, 2.5 M in hexane). This second solution was stirred for 1 hr, then added to the first solution dropwise over a period of 45 min. The resulting solution was stirred for 5 hr, then cooled in an ice bath. Isopropyllithium (43 mL, 30 mmol, 0.7 M in pentane) was added slowly, then stirring was continued for 12 hr. The reaction mixture was poured into 100 mL of a dilute ammonium chloride solution, then rinsed in with hexane (40 mL). The organic layer was separated, and the aqueous layer was extracted a second time (30 mL hexane). The organic layers were combined, washed with water (3×20 mL), dried over magnesium sulfate, filtered, and concentrated under vacuum to yield the crude product mixture. The product was isolated using chromatography on silica gel with hexane as an eluant (R$_f$~0.6 in hexane) and was concentrated to yield a colorless liquid (3.9 g, 6.0 mmol). To remove the trimethylsilyl-endcap, the product was taken up in THF (~15 mL) and methanol (~5 mL) and purged vigorously for 15 minutes. Purging was continued after the addition of 4 drops of a 15% aqueous sodium hydroxide solution. The reaction was allowed to stir with continued (but less vigorous) purging for 45 minutes. The mixture was extracted into hexane with the addition of water, washed with 10% hydrochloric acid solution (<5 mL) and water (3×20 mL), dried over magnesium sulfate, filtered, and concentrated under vacuum, to yield the product (3.4 g, 5.9 mmol, 39%) as a colorless liquid. Analysis of the colorless product provided the following data: $^1$H-NMR (200 MHz, CDCl$_3$) δ=2.4 (s, 1H), 2.2 (m, 2H), 1.0 (m, 14H), 0.8 (m, 2H).

Synthesis of 6,13-Bis(3,3,4,4,5,5,6,6,7,7,8,8,9,9,10,10,10-heptadecafluorodecyldiisopropylsilylethynyl)pentacene In an oven-dried 100-mL round bottom flask, 1.8 g of (3,3,4,4,5,5,6,6,7,7,8,8,9,9,10,10,10-heptadecafluorodecyldiisopropylsilyl)acetylene (3.1 mmol) was dissolved in anhydrous THF (5 mL). Isopropylmagnesium chloride (1.3 mL, 2.5 mmol, 2 M in THF) was added and the mixture was heated to 60° C. for 2 hr. After removing the reaction mixture from the heat, pentacene quinone (0.34 g, 1.1 mmol) was added and the flask was returned to heating at 60° C., which was continued for 12 hr. The reaction was quenched by the addition of 3 drops of a saturated ammonium chloride solution. Separately, a stannous chloride solution was made by dissolving stannous chloride dihydrate (0.90 g, 4.0 mmol) in 1.5 mL 10% aqueous hydrochloric acid, then this solution was added to the quenched reaction mixture. Stirring was continued for 10 min, then 50 mL methanol was added to precipitate the product, aided by refrigeration for 1 hr. The solid was collected by filtration, then taken up in hexane and rinsed onto a thick plug of silica gel. Hexane was flushed through the plug to elute excess acetylene, then the product was eluted using 8:1 hexane:dichloromethane. Solvent was removed to yield 0.25 g (0.17 mmol) as a blue solid, which recrystallized from ~15 mL acetone to yield 0.13 g (0.9 mmol, 8% from quinone) crystalline blue plates. Analysis of the product provided the following data: $^1$H-NMR (200 MHz, CDCl$_3$) δ=9.2 (s, 4H), 8.0 (dd, J=3.4 Hz, 6.6 Hz), 7.4 (dd, J=3.2 Hz, 7.0 Hz), 2.5 (m, 4H), 1.4 (m, 28H), 1.2 (m, 4H).

Example 6

Synthesis of 6,13-Bis-((3-heptafluoroisopropoxy)propyldiisopropylsilylethynyl)pentacene Synthesis of ((3-heptafluoroisopropoxy)propyldiisopropylsilyl)acetylene In a dried 250-mL round bottom flask, (3-heptafluoroisopropoxy)propyltrichlorosilane (4.87 g, 13.5 mmol) was dissolved in anhydrous THF (15 mL). The solution was cooled in an ice bath, and isopropyllithium (41 mL, 28 mmol, 0.7 M in pentane) was added dropwise over 1 hr, followed by warming to room temperature over 12 hr. Ethynylmagnesium bromide (35 mL, 17 mmol, 0.5 M in THF) was added and the solution was heated to 60° C. for 12 hr. The reaction was quenched by the slow addition of water, then dilute sulfuric acid was added to dissolve the magnesium salts. The mixture was extracted into hexane (2×50 mL), washed with water (5×10 mL), dried over magnesium sulfate, filtered, and concentrated. The product was purified using chromatography on silica gel with hexane as an eluant ($R_f$~0.6 in hexane), resulting in 2.4 g (6.5 mmol, 48%) of a colorless liquid. Analysis of the colorless product provided the following data: $^1$H-NMR (200 MHz, CDCl$_3$) δ=4.0 (t, J=6.2 Hz, 2H), 2.4 (s, 1H), 1.8 (m, 2H), 1.0 (m, 14H), 0.6 (m, 2H).

Synthesis of 6,13-Bis-((3-heptafluoroisopropoxy) propyldiisopropylsilylethynyl)-pentacene In an oven-dried 100-mL round bottom flask, ((3-heptafluoroisopropoxy)-propyldiisopropylsilyl)acetylene (2.0 g, 5.4 mmol) was dissolved in anhydrous THF (5 mL), then cooled in an ice bath. n-Butyllithium (1.8 mL, 4.5 mmol, 2.5 M in hexane) was added dropwise, and the solution was stirred in the bath for 30 minutes. Pentacene quinone (0.57 g, 1.8 mmol) was added, and the reaction was stirred for 12 hr. In a separate Erlenmeyer flask, stannous chloride dihydrate (1.4 g, 6.4 mmol) was dissolved in methanol (100 mL), and 1 mL of a 10% hydrochloric acid solution was added, then this solution was refrigerated for 1 hr. The reaction mixture was quenched by the addition of 0.5 mL of a saturated ammonium chloride solution, then diluted with methanol (20 mL). The quenched reaction mixture was poured in a slow stream into the stannous chloride mixture with stirring, and rinsed in with additional methanol. Stirring was continued for 30 minutes, then the entire mixture was refrigerated for 3 hr. The solid was removed by filtration, dried in ambient atmosphere, then purified using chromatography on silica gel with 9:1 hexane: dichloromethane as an eluant to yield 0.68 g of a blue solid. Recrystallization from acetone (~30 mL) yielded 0.6 g (0.6 mmol, 34%) product as burgundy plates. Analysis of the colorless product provided the following data: $^1$H-NMR (200 MHz, CDCl$_3$) δ=9.2 (s, 4H), 7.9 (dd, J=3.4 Hz, 7.0 Hz, 4H), 7.4 (dd, J=3.4 Hz, 7.0 Hz, 4H), 4.1 (t, J=6.0 Hz, 4H), 2.1 (m, 4H), 1.3 (m, 28H), 1.0 (m, 4H).

Examples 7-10

Preparation of Thin Film Transistors by Dip-Coating Solutions of 6,13-bis(3,3,3-trifluoropropyldiisopropylsilylethynyl)pentacene Four solutions of 6,13-bis(3,3,3-trifluoropropyldiisopropylsilylethynyl)pentacene and optionally polystyrene as described in Table 3 were prepared by the following method. An amount of 6,13-bis(3,3,3-trifluoropropyldiisopropylsilylethynyl)pentacene and an optional amount of polystyrene were weighed into an amber glass vial containing a magnetic stir bar followed by the weighed addition of solvent(s) (n-butylbenzene (nbb), anisole, or decane) to prepare a composition of the desired concentrations of organic semiconductor, 6,13-bis(3,3,3-trifluoropropyl-diisopropylsilylethynyl)pentacene, and optional polystyrene in the composition and the desired weight ratio of solvents for compositions that contained more than one solvent. The vial was capped, and then placed on a stir plate and the contents stirred. The vial was covered with a metal can to shield the composition from light. The contents were stirred for a minimum of 12 hours.

Each semiconductor solution was filtered through a polytetrafluoroethylene (PTFE) filter with a pore size of 0.2 micron and 25 mm diameter that is commercially available under the trade designation ACRODISC® CR from Pall Life Sciences (East Hills, N.Y.) and then placed in a dip-coating tank (approximately 50 mm wide, 5 mm deep, and 30 mm high). Approximately 5 mL of each solution was used. One substrate of an n-type silicon wafer with thermal oxide (a silicon <100> wafer highly doped n+ (arsenic) with a resistivity of <0.005 ohm-cm, and supplied with a 1000 Angstrom thermal oxide (SiO$_2$) on the front surface and coated with 100 Angstrom TiN and 5000 Angstrom aluminum on the back surface from Noel Technologies, Inc. (Campbell, Calif.) was dip-coated per solution/composition. Each substrate was treated for 3 minutes in a Plasma Cleaning System (Model YES-G1000 from Yield Engineering Systems, Inc. (Livermore, Calif.)) using a power setting of 500 Watts and oxygen pressure of approximately 200 milli-Torr prior to dip-coating. Each substrate sample was dipped at a draw rate of approximately 3 millimeters per minute using a dip coating apparatus that is commercially available under the trade designation NIMA D1L from Nima Technology Ltd. (Coventry, United Kingdom). Each sample was allowed to dry at room temperature.

After coating, long crystals were present on the SiO$_2$ surface of the substrate, and typically oriented parallel to the dip axis. That is, the long dimension of the crystals ran in the same direction as the dip direction. Gold source and drain electrodes (approximately 800-1000 Angstroms thick) were vapor deposited through a shadow mask using a thermal evaporator, thus forming transistors with a bottom gate, top contact architecture. Source and drain electrodes were oriented with the long dimension of the electrodes, the channel width, perpendicular to the dip axis. The channel length was approximately 100 micrometers. The mobilities of 10 transistors on each substrate were determined by Mobility Value Test Method II and the average is given in Table 4.

TABLE 4

Average Charge Carrier Mobility Values Using Mobility Value Test Method II

| Example | Wt. % Semi-conductor | Wt. % Polystyrene | Solvent | Charge Carrier Mobility Value (cm$^2$/V-s) |
|---|---|---|---|---|
| 7 | 2 | 0 | nbb | 0.0105 |
| 8 | 2 | 0 | 91/9 w/w nbb/decane | 0.0119 |
| 9 | 2 | 1 | 91/9 w/w nbb/decane | 0.0956 |
| 10 | 2 | 0 | 91/9 w/w anisole/decane | 0.0359 |

Example 11

Preparation of Thin Film Transistors by Knife Coating Solution of 6,13-Bis(3,3,4,4,5,5,6,6,7,7,8,8,9,9, 10,10,10-heptadecafluorodecyldiisopropylsilylethynyl)-pentacene 6,13-Bis(3,3,4,4,5,5,6,6,7,7,8,8,9,9,10,10,10-heptadecafluorodecyldiisopropylsilylethynyl)pentacene (0.0234 g) was added to a glass vial, and then 3-(trifluoromethyl)anisole (1.3016 g) was added to the vial. The vial was capped, and then wrapped with aluminum foil to shield the composition from light. The vial stood for a couple of hours and then was placed on an IKA LABORTECHNIK HS501 shaker (IKA Werke GmbH & Co. KG (Staufen, Germany)) and shaken for approximately 48 hours. The contents of the vial were filtered through a polytetrafluoroethylene (PTFE) filter with a pore size of 0.2 micron and 25 mm diameter that is commercially available under the trade designation ACRODISC® CR from Pall Life Sciences (East Hills, N.Y.).

A piece of n-type silicon wafer with thermal oxide (a 4 inch diameter silicon <100> wafer, which was highly doped n+ (arsenic) with a resistivity of <0.005 ohm-cm and supplied with a 1000 Angstrom thermal oxide ($SiO_2$) on the front surface and coated with 100 Angstrom TiN and 5000 Angstrom aluminum on the back surface from Noel Technologies, Inc. (Campbell, Calif.) was cleaved approximately into sixths to yield the piece) was treated for 4 minutes in a Plasma Cleaning System (Model YES-G1000 from Yield Engineering Systems, Inc. (Livermore, Calif.)) using a power setting of 500 Watts and oxygen pressure of approximately 200 milliTorr prior to knife coating of the semiconductor solution.

The knife coater blade was placed approximately 0.005 inches above the thermal oxide surface of the piece of silicon wafer, and a disposable glass pipette was used to place a small bead of the semiconductor solution between the blade and the thermal oxide surface. The knife coater was then drawn by hand over the wafer to coat the wafer with the semiconductor solution. Immediately after knife coating the semiconductor solution, the solution-coated wafer was covered with a glass petri dish (approximately 90 mm diameter×15 mm deep) to slow the solvent, 3-(trifluoromethyl)anisole, evaporation. The sample was left to dry at room temperature in extremely dim room light.

After approximately 3 hours, the sample was dry. Gold source and drain electrodes (approximately 1000 Angstroms thick) were vapor deposited through a shadow mask onto the semiconductor layer using a thermal evaporator, thus forming transistors with a bottom gate, top contact architecture. Source and drain electrodes were oriented with the long dimension of the electrodes, the channel width, perpendicular to the knife coating direction. The channel length was approximately 100 micrometers. The mobilities of 9 transistors were determined by Mobility Value Test Method I and the average was $1.20 \times 10^{-3}$ $cm^2/V$-s.

Example 12

Synthesis of 6,13-Bis(3,3,4,4,5,5,6,6,7,7,8,8,8-tridecafluorooctyldimethylsilylethynyl)pentacene Using a Second Method In an oven-dried 100-mL round bottom flask, (3,3,4,4,5,5,6,6,7,7,8,8,8-tridecafluorooctyldimethylsilyl)acetylene (2.4 g, 5.6 mmol) (as synthesized in Example 4) was dissolved in toluene (10 mL). Isopropylmagnesium chloride (2.4 mL, 2 M in THF) was added dropwise, and the solution was heated to 60° C. for 1 hr. Anhydrous THF (6 mL) was added and the solution became homogeneous. The mixture was removed from the heat and pentacene quinone (0.63 g, 2.0 mmol) was added. Heating at 60° C. was resumed and continued for 12 hr. The homogeneous reaction mixture was cooled to room temperature, then quenched by the addition of 0.5 mL of a saturated solution of ammonium chloride. In a separate Erlenmeyer flask with stir bar, stannous chloride dihydrate (7.0 mmol, 1.6 g) was dissolved in methanol (150 mL), and then 2 mL 10% HCl was added. After cooling the methanol solution for 1 hr, the reaction mixture was diluted with methanol (50 mL), then rinsed into the Erlenmeyer flask with additional methanol (20 mL), and allowed to stir for 15 min at room temperature. This mixture was cooled for 1 hr. The solid was collected by filtration, rinsed with methanol, and dried in ambient atmosphere. This solid was taken up in minimal DCM, diluted with hexane (about 9:1 hexane:DCM), then rinsed onto a medium pad of silica gel and eluted with 9:1 hexane:DCM. Removal of solvent yielded 0.95 g of a shiny blue solid, that was recrystallized twice from acetone to yield 0.80 g (0.70 mmol, 35% from the quinone) of blue needles. Analysis of the product provided the following data: $^1$H-NMR (200 MHz, $CDCl_3$) δ=9.1 (s, 4H), 8.0 (dd, J=3.3 Hz, 6.6 Hz, 4H), 7.4 (dd, J=3.3 Hz, 6.6 Hz, 4H), 2.4 (m, 4H), 1.2 (m, 4H), 0.6 (s, 12H).

Example 13

Synthesis of 6,13-Bis(3,3,4,4,5,5,6,6,7,7,8,8,8-tridecafluorooctyldiisopropylsilylethynyl)pentacene Synthesis of (3,3,4,4,5,5,6,6,7,7,8,8,8-tridecafluorooctyldiisopropylsilyl)acetylene Using a First Method In an oven-dried 250-mL round bottom flask, 3,3,4,4,5,5,6,6,7,7,8,8,8-tridecafluorooctyltrichlorosilane (9.8 g, 21.2 mmol) was dissolved in anhydrous THF (14 mL). In a separate oven-dried 100-mL round bottom flask, trimethylsilylacetylene (2.5 g, 25 mmol) was dissolved in anhydrous THF (18 mL) and cooled in an ice bath, followed by the dropwise addition of n-butyllithium (8.4 mL, 21 mmol, 2.5 M in hexane). This second solution was stirred for 1 hr, and then added to the first solution dropwise over a period of 45 min. The resulting solution was stirred for 5 hr, and then cooled in an ice bath. Isopropyllithium (66 mL, 46 mmol, 0.7 M in pentane) was added slowly, and then stirring was continued for 12 hr. The reaction mixture was poured into 100 mL of a dilute ammonium chloride solution, and then rinsed in with hexane (40 mL). The organic layer was separated, and the aqueous layer was extracted a second time (30 mL hexane). The organic layers were combined, washed with water (3×20 mL), dried over $MgSO_4$, filtered, and concentrated under vacuum to yield the crude product mixture as a light brown liquid. The product was isolated using chromatography on silica gel with hexane as an eluant ($R_f$~0.6 in hexane) and was concentrated to yield a colorless liquid (4.9 g, 8.8 mmol). To remove the trimethylsilyl-endcap, the product was taken up in THF (~15 mL) and methanol (~5 mL), and treated with 15% aqueous sodium hydroxide solution (10 drops). After stirring for 1 hr., the mixture was extracted into hexane with the addition of water, washed with 10% HCl (5 mL) and water (3×20 mL), dried over $MgSO_4$, filtered, and concentrated under vacuum to yield the product (4.2 g, 8.7 mmol, 41%) as a colorless liquid. Analysis of the product provided the following data: $^1$H-NMR (200 MHz, $CDCl_3$) δ=2.4 (s, 1H), 2.2 (m, 2H), 1.0 (m, 14H), 0.8 (m, 2H).

Synthesis of (3,3,4,4,5,5,6,6,7,7,8,8,8-tridecafluorooctyldiisopropylsilyl)acetylene Using a Second Method In an oven-dried round-bottom flask equipped with a stir bar and cooled under $N_2$, 3,3,4,4,5,5,6,6,7,7,8,8,8-tridecafluorooctyldiisopropylsilane (1.9 g, 4.1 mmol) was dissolved in 12 mL anhydrous benzene (benzene dried by boiling off 10% by volume prior to use). To this mixture was added allyl bromide (0.76 g, 6.3 mmol, 1.5 eq.) and $PdCl_2$ (30 mg). The solution was heated to 60° C. for 15 hr, then cooled and concentrated via rotary evaporation. The resulting suspension was dissolved in pentane and filtered to remove residual catalyst, then solvent was removed to yield (3,3,4,4,5,5,6,6,7,7,8,8,8-tridecafluorooctyldfisopropylsilyl)bromide (2.0 g) as a pale brown liquid. The bromide was treated under anhydrous conditions with 1.2 eq. (based on initial silane) of ethynylmagnesium bromide and heated to 40° C. for 6 hr. The reaction was quenched with water and dilute sulfuric acid, pentane was added, and the organic layer was separated. The organic layer was washed with water (6×50 mL), dried over MgSO$_4$, filtered, and concentrated via rotary evaporation. Further purification via flash chromatography using hexane yielded pure (3,3,4,4,5,5,6,6,7,7,8,8,8-tridecafluorooctyldiisopropylsilyl)acetylene (1.5 g, 3.1 mmol, 77%) as a colorless liquid.

Synthesis of 6,13-Bis(3,3,4,4,5,5,6,6,7,7,8,8,8-tridecafluorooctyldiisopropylsilylethynyl)pentacene In an oven-dried round bottom flask, (3,3,4,4,5,5,6,6,7,7,8,8,8-tridecafluorooctyldiisopropylsilyl)acetylene (1.4 g, 2.9 mmol) (prepared from either of the first and second methods above) was dissolved in hexane (20 mL) and treated with n-butyllithium (0.9 mL, 2.3 mmol, 2.5 M in hexane) dropwise at 0° C. The solution was allowed to warm to room temperature over 1 hr, and then pentacene quinone (0.22 g, 0.70 mmol) was added. Stirring was continued for 15 hr, and then the reaction was quenched by the addition of a saturated ammonium chloride solution (10 mL). Reaction grade THF (25 mL), stannous chloride dihydrate (2 g), and 10% HCl (6 mL) were added and the mixture was stirred vigorously for 30 min. Hexane was added and the organic layer was separated, then washed with 10% HCl (2×10 mL) and water (2×10 mL), dried over MgSO$_4$, and filtered through a thin pad of silica (5:1 hexane:DCM). Solvent was removed via rotary evaporation and the resulting blue oil was taken up in hexane and flushed onto a thick pad of silica. Hexane (200 mL) was used to elute excess acetylene, and then the product was eluted using 9:1 hexane:DCM. Removal of solvent yielded 0.55 g of blue solid, which was recrystallized from acetone (20 mL) to yield small blue needles (0.35 g, 0.28 mmol, 40% from quinone). Analysis of the product provided the following data: $^1$H-NMR (400 MHz, CDCl$_3$) δ=9.2 (s, 4H), 7.9 (dd, J=6.4 Hz, 3.2 Hz, 4H), 7.4 (dd, J=6.8 Hz, 2.8 Hz, 4H), 2.5 (m, 4H), 1.4 (m, 28H), 1.2 (m, 4H).

Example 14

Synthesis of 6,13-Bis(3,3,4,4,5,5,6,6,6-nonafluorohexyldiisopropylsilylethynyl)pentacene Synthesis of (3,3,4,4,5,5,6,6,6-nonafluorohexyldiisopropylsilyl)acetylene In an oven-dried round-bottom flask equipped with a stir bar and cooled under N$_2$, 3,3,4,4,5,5,6,6,6-nonafluorohexyldiisopropylsilane (10.1 g, 27.8 mmol) was dissolved in allyl bromide (20 mL), and PdCl$_2$ (50 mg) was added. The solution was heated to 60° C. for 15 hr, then cooled, and concentrated via rotary evaporation. The resulting suspension was dissolved in pentane, filtered to remove residual catalyst, and then solvent was removed to yield (3,3,4,4,5,5,6,6,6-nonafluorohexyldiisopropylsilyl)bromide (12.1 g) as a pale brown liquid. The bromide was treated under anhydrous conditions with 1.2 eq. (based on initial silane) of ethynylmagnesium bromide and heated to 40° C. for 6 hr. The reaction was quenched with water and dilute sulfuric acid, pentane was added, and the organic layer was separated. The organic layer was washed with water (6×50 mL), dried over MgSO$_4$, filtered, and concentrated via rotary evaporation. Further purification via flash chromatography using hexane yielded pure (3,3,4,4,5,5,6,6,6-nonafluorohexyldiisopropylsilyl)acetylene (9.90 g, 25.6 mmol, 92%) as a colorless liquid. Analysis of the product provided the following data: $^1$H-NMR (200 MHz, CDCl$_3$) δ=2.4 (s, 1H), 2.2 (m, 2H), 1.1 (m, 14H), 0.8 (m, 2H).

Synthesis of 6,13-Bis(3,3,4,4,5,5,6,6,6-nonafluorohexyldiisopropylsilylethynyl)-pentacene In an oven-dried 100-mL round bottom flask, (3,3,4,4,5,5,6,6,6-nonafluorohexyldiisopropylsilyl)acetylene (1.1 g, 2.9 mmol) was dissolved in hexane (15 mL), and then cooled in an ice bath. n-Butyllithium (0.8 mL, 2.0 mmol, 2.5 M in hexane) was added dropwise, and then stirring was continued for 1 hr. Pentacene quinone (0.22 g, 0.7 mmol) was added, and the reaction mixture was stirred for 12 hr. The reaction was quenched by the addition of saturated ammonium chloride solution (10 mL), and then reaction grade THF (20 mL), stannous chloride dihydrate (1.3 g) and 10% HCl (6 mL) were added. After stirring for 30 minutes, hexane (20 mL) was added, and the organic layer was separated. The organic layer was washed with 10% HCl (2×10 mL) and water (2×10 mL), then dried over MgSO$_4$, and rinsed through a thin pad of silica using 5:1 hexane:DCM as an eluant. Solvent was removed, and the resulting blue oil was taken up in hexane and rinsed onto a thick pad of silica. Excess acetylene was eluted using hexane, and then the product was eluted using 9:1 hexane:DCM. Concentration under vacuum yielded 0.52 g of a blue solid, which was recrystallized from dichloroethane (~8 mL) to yield 0.24 g (0.23 mmol, 33% from quinone) of burgundy plates. Analysis of the product provided the following data: $^1$H-NMR (200 MHz, CDCl$_3$) δ=9.2 (s, 4H), 8.0 (dd, J=3.0 Hz, 6.6 Hz, 4H), 7.4 (dd, J=3.2 Hz, 7.0 Hz, 4H), 2.5 (m, 4H), 1.3 (m, 28H), 0.8 (m, 4H).

Example 15

Synthesis of 6,13-Bis(3,3,4,4,5,5,6,6,7,7,8,8,9,9,10,10,10-heptadecafluorodecyldiisopropylsilylethynyl) pentacene Synthesis of (3,3,4,4,5,5,6,6,7,7,8,8,9,9,10,10,10-heptadecafluorodecyldiisopropylsilyl)acetylene In an oven-dried round-bottom flask equipped with a stir bar and cooled under N$_2$, 3,3,4,4,5,5,6,6,7,7,8,8,9,9,10,10,10-heptadecafluorodecyldiisopropylsilane (9.97 g, 17.7 mmol) was dissolved in 15 mL anhydrous benzene (benzene dried by boiling off 10% by volume prior to use). To this was added allyl bromide (3.22 g, 26.6 mmol, 1.5 eq.) and PdCl$_2$ (35 mg, 1 mol %). The solution was heated to 60° C. for 15 hr, then cooled, and concentrated via rotary evaporation. The resulting suspension was dissolved in pentane, filtered to remove residual catalyst, and then solvent was removed to yield (3,3,4,4,5,5,6,6,7,7,8,8,9,9,10,10,10-heptadecafluorodecyldiisopropylsilyl)bromide (11.3 g) as a pale brown liquid. The bromide was treated under anhydrous conditions with 1.2 eq. (based on initial silane) of ethynylmagnesium bromide and heated to 40° C. for 6 hr. The reaction was quenched with water and dilute sulfuric acid, pentane was added, and the organic layer was separated. The organic layer was washed with water (6×50 mL), dried over MgSO$_4$, filtered, and concentrated via rotary evaporation. Further purification via flash chromatography using hexane yielded pure (3,3,4,4,5,5,6,6,7,7,8,8,9,9,10,10,10-heptadecafluorodecyl-diisopropylsilyl)acetylene (9.0 g, 15 mmol, 87%) as a colorless liquid. Analysis of the product provided the following data: $^1$H-NMR (200 MHz, CDCl$_3$) δ=2.4 (s, 1H), 2.2 (m, 2H), 1.0 (m, 14H), 0.8 (m, 2H).

Synthesis of 6,13-Bis(3,3,4,4,5,5,6,6,7,7,8,8,9,9,10,10,10-heptadecafluorodecyldiisopropylsilylethynyl)pentacene Pentacene synthesis was conducted in same fashion as described in Example 5, except employing acetylene synthesized by the above procedure of this example. Analysis of the product provided the following data: $^1$H-NMR (200 MHz, CDCl$_3$) δ=9.2 (s, 4H), 8.0 (dd, J=3.4 Hz, 6.6 Hz), 7.4 (dd, J=3.2 Hz, 7.0 Hz), 2.5 (m, 4H), 1.4 (m, 28H), 1.2 (m, 4H).

Example 16

Synthesis of 6,13-Bis((3,3,4,4,5,5,6,6,7,7,8,8,9,10,10,10-hexadecafluoro-9-trifluoromethyldecyl)diisopropylsilylethynyl)pentacene Synthesis of ((3,3,4,4,5,5,6,6,7,7,8,8,9,10,10,10-hexadecafluoro-9-trifluoromethyldecyl)diisopropylsilyl)acetylene In an oven-dried round-bottom flask equipped with a stir bar and cooled under N$_2$, (3,3,4,4,5,5,6,6,7,7,8,8,9,10,10,10-hexadecafluoro-9-trifluoromethyldecyl)diisopropylsilane (4.86 g, 7.94 mmol) was dissolved in 10 mL anhydrous benzene (benzene dried by boiling off 10% by volume prior to use). To this mixture was added allyl bromide (1.44 g, 11.9 mmol, 1.5 eq.) and PdCl$_2$ (30 mg). The solution was heated to 60° C. for 15 hr, then cooled, and concentrated via rotary evaporation. The resulting suspension was dissolved in pentane, filtered to remove residual catalyst, and then solvent was removed to yield ((3,3,4,4,5,5,6,6,7,7,8,8,9,10,10,10-hexadecafluoro-9-trifluoromethyldecyl)diisopropylsilyl)-bromide (11.3 g) as a pale brown liquid. The bromide was treated under anhydrous conditions with 1.2 eq. (based on initial silane) of ethynylmagnesium bromide and heated to 40° C. for 6 hr. The reaction was quenched with water and dilute sulfuric acid, pentane was added, and the organic layer was separated. The organic layer was washed with water (6×50 mL), dried over MgSO$_4$, filtered, and concentrated via rotary evaporation. Further purification via flash chromatography using hexane yielded pure ((3,3,4,4,5,5,6,6,7,7,8,8,9,10,10,10-hexadecafluoro-9-trifluoromethyldecyl)diisopropylsilyl)-acetylene (4.1 g, 6.5 mmol, 82%) as a colorless liquid. Analysis of the product provided the following data: $^1$H-NMR (200 MHz, CDCl$_3$) δ=2.4 (s, 1H), 2.2 (m, 2H), 1.0 (m, 14H), 0.8 (m, 2H).

Synthesis of 6,13-Bis((3,3,4,4,5,5,6,6,7,7,8,8,9,10,10,10-hexadecafluoro-9-trifluoromethyldecyl)diisopropylsilylethynyl)pentacene In an oven dried round bottom flask, ((3,3,4,4,5,5,6,6,7,7,8,8,9,10,10,10-hexadecafluoro-9-trifluoromethyldecyl)diisopropylsilyl)acetylene (0.64 g, 1.0 mmol) was dissolved in hexane (10 mL) and treated at 0° C. with n-butyllithium (0.28 mL, 0.7 mmol, 2.5 M in hexane). After 1 hr, pentacene quinone (77 mg, 0.25 mmol) was added and stirring was continued for 15 hr. Anhydrous THF (10 mL) was added, upon which the solution became uniform, and stirring was continued for 1 hr. The reaction was quenched by the addition of saturated ammonium chloride solution (10 mL). Reaction grade THF (10 mL), stannous chloride dihydrate (1.0 g, 4.4 mmol) and 10% HCl (6 mL) were added, and vigorous stirring was continued for 30 min. Hexane was added and the organic layer was separated, washed with 10% HCl (2×10 mL) and water (2×10 mL), dried over MgSO$_4$, and rinsed through a thin pad of silica (5:1 hexane:DCM). Solvent was removed to yield the crude pentacene, which was taken up in hexane (50 mL), and rinsed onto a thick pad of silica. The silica was flushed with hexane to elute the excess acetylene, and then the product was eluted using 9:1 hexane:DCM. Removal of solvent yielded 0.16 g of crude blue solid, which was recrystallized from dichloroethane (10 mL) to yield pure product as small blue needles (0.10 g, 0.065 mmol, 26%). Analysis of the product provided the following data: $^1$H-NMR (400 MHz, CDCl$_3$) δ=9.2 (s, 4H), 7.9 (dd, J=6.4 Hz, 3.2 Hz, 4H), 7.4 (dd, J=6.8 Hz, 3.2 Hz, 4H), 2.5 (m, 4H), 1.4 (m, 28H), 1.2 (m, 4H).

Example 17

Synthesis of 6,13-Bis(3,3,4,4,5,5,6,6,7,7,8,8,9,9,10,10,10-heptadecafluorodecyldiisopropylsilylethynyl)-2,3,9,10-tetramethylpentacene Synthesis of 2,3,9,10-tetramethylpentacene-6,13-dione To 1.6 grams (10 mmol) of 4,5-dimethyl phthalaldehyde in 20 mL ethanol was added 0.56 grams (5 mmol) of cyclohexane-1,4-dione. Upon complete dissolution of the starting materials, 2 drops of 15% aq. NaOH solution were added, and precipitation of the quinone began immediately. The suspension was stirred for a further 2 hours, then diluted with a 10-fold excess of methanol, and the solid collected by filtration. The solid quinone was washed with copious methanol, then ether, and was allowed to air-dry overnight. The quinone (1.5 g, 82%) was used without further purification.

Synthesis of 6,13-Bis(3,3,4,4,5,5,6,6,7,7,8,8,9,9,10,10,10-heptadecafluorodecyldiisopropylsilylethynyl)-2,3,9,10-tetramethylpentacene (3,3,4,4,5,5,6,6,7,7,8,8,9,9,10,10,10-heptadecafluorodecyldiisopropylsilyl)acetylene (1.8 g, 3.0 mmol) from Example 15 above was added to an oven-dried round bottom flask and dissolved in hexane (20 mL). After cooling to 0° C., the solution was treated with n-butyllithium (1.0 mL, 2.5 mmol, 2.5 M in hexane) dropwise, and stirring was continued for 1 hr. 2,3,9,10-tetramethylpentacene-6,13-dione (0.28 g, 0.80 mmol) was added, followed by the addition of anhydrous THF (3 mL) after 10 min. The reaction was allowed to continue for 15 hr, resulting in a homogeneous solution. To this solution was added saturated ammonium chloride solution (20 mL), reaction grade THF (30 mL), stannous chloride dihydrate (3 g), and 10% HCl (25 mL), followed by vigorous stirring for 30 min. After adding hexane (20 mL), the organic layer was separated, washed with 10% HCl (2×10 mL) and water (2×10 mL), dried over MgSO$_4$, and rinsed through a thin pad of silica (1:1 hexane:DCM). Removal of solvent yielded a blue oil, which was taken up in hexane and rinsed onto a thick pad of silica. Additional hexane was rinsed through the silica to elute excess acetylene, and then the product was eluted using 7:1 hexane:DCM. Removal of solvent yielded a blue solid, which was recrystallized from ~1:1 heptane:toluene, providing the product as a fibrous mass of tiny blue needles (0.3 g, 0.2 mmol, 25% from quinone).

Analysis of the product provided the following data: $^1$H-NMR (400 MHz, CDCl$_3$) δ=9.0 (s, 4H), 7.7 (s, 4H), 2.6 (m, 4H), 2.5 (s, 12H), 1.3 (m, 28H), 1.2 (m, 4H). $^{13}$C-NMR (400 MHz, CDCl$_3$) δ=137, 132, 131, 125, 124, 118, 107, 104, many inseparable peaks between 21 and 18, 12.

Example 18

Synthesis of 6,13-Bis(3,3,4,4,5,5,5-heptafluoropentyldiisopropylsilylethynyl)-pentacene Synthesis of (3,3,4,4,5,5,5-heptafluoropentyldiisopropylsilyl)acetylene In an oven dried round bottom flask, (3,3,4,4,5,5,5-heptafluoropentyl)diisopropylsilane (10 g, 32 mmol) was dissolved in allyl bromide (20 mL) and the flask was flushed with N$_2$. PdCl$_2$ (40 mg) was added and the solution was heated to 60° C. for 12 hr. Solvent was removed on a rotary evaporator to yield a brown suspension that was taken up in pentane and filtered. Solvent removal yielded the bromosilane as a brown liquid (12.1 g). The bromosilane, (3,3,4,4,5,5,5-heptafluoropentyldiisopropylsilyl)bromide, was treated with ethynylmagnesium bromide (70 mL, 35 mmol, 0.5 M in THF) in anhydrous THF (20 mL) and heated to 40° C. for 4 hr. After cooling, the reaction was quenched by the slow addition of water (20 mL) and dilute sulfuric acid sufficient to dissolve the magnesium salts. Pentane was added and the organic layer was separated. The aqueous layer was extracted with pentane an additional time, then the organic layers were combined, washed with water (5×10 mL) and brine, dried over MgSO$_4$, and filtered. Solvent was removed and the crude product was taken up in hexane and rinsed through a thin pad of silica. Solvent removal yielded the product as a colorless liquid (9.7 g, 29 mmol, 90%). Analysis of the product provided the following data: $^1$H-NMR (400 MHz, CDCl$_3$) δ=2.4 (s, 1H), 2.2 (m, 2H), 1.0 (m, 14H), 0.8 (m, 2H).

Synthesis of 6,13-Bis(3,3,4,4,5,5,5-heptafluoropentyldiisopropylsilylethynyl)-pentacene (3,3,4,4,5,5,5-heptafluoropentyldiisopropylsilyl)acetylene (1.9 g, 5.7 mmol) was dissolved in hexane in an oven-dried round-bottom flask, and treated with n-butyllithium (1.9 mL, 4.2 mmol, 2.5 M in hexane) dropwise at 0° C. After 1 hr of stirring, pentacene quinone (0.52 g, 1.7 mmol) was added, and stirring was continued for 15 hr followed by the addition of anhydrous THF (15 mL) and an additional 2 hr of stirring. Saturated ammonium chloride solution (15 mL), stannous chloride dihydrate (4 g), and 10% HCl (15 mL) were added, and the resulting solution was stirred vigorously for 30 min. Hexane (30 mL) was added, the organic layer was separated, then washed with 10% HCl (2×10 mL) and water, dried over MgSO$_4$, and flushed through a thin pad of silica using 5:1 hexane:DCM. Solvent was removed, the resulting blue oil was taken up in hexane and rinsed onto a thick pad of silica, which was then flushed with hexane (200 mL) to elute excess acetylene. The product was eluted using 9:1 hexane:DCM, and then solvent was removed to yield a blue solid. The crude product was recrystallized from acetone (25 mL) to yield the pure product as burgundy plates (0.91 g, 0.97 mmol, 57% relative to quinone). Analysis of the product provided the following data: H-NMR (400 MHz, CDCl$_3$) δ=9.2 (s, 4H), 7.9 (dd, J=6.4 Hz, 3.2 Hz, 4H), 7.4 (dd, J=6.4 Hz, 3.2 Hz, 4H), 2.5 (m, 4H), 1.4 (m, 28H), 1.2 (m, 4H).

Example 19

Synthesis of 6,13-Bis(3,3,4,4,5,5,6,6,6-nonafluorohexyldiisopropylsilylethynyl)-1-fluoropentacene Synthesis of 1-Fluoropentacene-6,13-dione 3-Fluoro-o-xylene (1.2 g, 9.7 mmol) was added to a round-bottom flask with a stir bar and dissolved in 30 mL dichloroethane. N-Bromosuccinimide (7.0 g, 39 mmol) and a small scoop of AIBN were added, a reflux condenser was attached, and the mixture was refluxed for 6 hr, at which point analysis by GC-MS showed the predominant component to be the tribrominated product. After cooling, water and dichloromethane were added, and the organic layer was separated, then washed with water and dilute hydrochloric acid, dried over MgSO$_4$, and rinsed through a thin pad of silica gel using dichloromethane as an eluant. Removal of solvent yielded 3.4 g of a product mixture. To a 100 mL round-bottom flask equipped with a condenser and stir bar, 12 mL dimethylformamide was added, followed by 0.54 g (2.07 mmol) of the tribrominated product from above and 0.43 g (2.1 mmol) 1,4-anthraquinone. Nitrogen was bubbled through the solution for 20 minutes, then 2.1 g (12 mmol) potassium iodide was added, and the reaction was heated at 110° C. for 3 days. The reaction was allowed to cool, and the precipitate was collected by filtration, then rinsed sequentially with water, acetone and diethyl ether. The resulting solid was air-dried, yielding 0.29 g (0.88 mmol, 42%) of 1-fluoropentacene-6,13-dione (or 1-fluoropentacenequinone) as a light brown solid.

Synthesis of 6,13-Bis(3,3,4,4,5,5,6,6,6-nonafluorohexyldiisopropylsilylethynyl)-1-fluoropentacene In a cooled oven-dried flask, (3,3,4,4,5,5,6,6,6-nonafluorohexyldiisopropylsilyl)acetylene (1.1 g, 3.0 mmol) from Example 14 was dissolved in hexane (15 mL) and cooled in an ice bath. n-Butyllithium (0.96 mL, 2.4 mmol, 2.5 M in hexane) was added dropwise and the solution was allowed to warm to room temperature over 1 hr. 1-fluoropentacene-6,13-dione (0.28 g, 0.85 mmol) was added and stirring was continued overnight. The reaction was quenched by the addition of saturated ammonium chloride solution (10 mL), then reagent-grade THF (10 mL), stannous chloride dihydrate (1.5 g), and 10% HCl were added, and the reaction was stirred vigorously for 1 hr. Hexane was added, and the organic layer was separated, washed with 10% HCl (2×10 mL) and water (10 mL), then dried over MgSO$_4$, and rinsed onto a thin pad of silica. The crude product was eluted using 5:1 hexane:DCM, and solvent was removed on a rotary evaporator. The resulting blue oil was taken up in hexane and rinsed onto a thick pad of silica. Additional hexane was rinsed through the silica to elute excess acetylene, and then the product was eluted using 9:1 hexane:DCM. Removal of solvent yielded 0.28 g of a blue solid, which was recrystallized from ethanol:chloroform (15 mL:2 mL) to yield 0.20 g (0.20 mmol, 24% from quinone) of burgundy plates. Analysis of the product provided the following data: H-NMR (400 MHz, CDCl$_3$) δ=9.5 (s, 1H), 9.2 (s, 1H), 9.2 (s, 2H), 7.9 (m, 2H), 7.7 (d, J=8.8 Hz, 1H), 7.4 (dd, J=6.8, 3.2 Hz, 1H), 7.2 (m, 1H), 7.0 (m, 1H), 2.5 (m, 4H), 1.4 (m, 28H), 1.2 (m, 4H).

Example 20

Synthesis of 6,13-Bis(3,3,4,4,5,5,6,6,6-nonafluorohexyldiisopropylsilylethynyl)-2,3,9,10-tetramethylpentacene In a cooled oven-dried flask, (3,3,4,4,5,5,6,6,6-nonafluorohexyldiisopropylsilyl)acetylene (1.5 g, 4.2 mmol) from Example 14 was dissolved in hexane (20 mL) and cooled in an ice bath. n-Butyllithium (1.4 mL, 3.4 mmol, 2.5 M in hexane) was added dropwise and the solution was allowed to warm to room temperature over 1 hr. 2,3,9,10-tetramethylpentacene-6,13-dione (0.44 g, 1.2 mmol) from Example 17 was added, stirring was continued for 20 min., followed by the addition of anhydrous THF (3 mL). After 12 hr, additional anhydrous THF (15 mL) was added and a pale yellow suspension remained. The reaction was quenched by the addition of saturated ammonium chloride solution (15 mL), then stannous chloride dihydrate (3 g) and 10% HCl (10 mL) were added, and the reaction mixture was stirred vigorously for 1 hr. Hexane was added, and the organic layer was separated, washed with 10% HCl (2×10 mL) and water (10 mL), then dried over $MgSO_4$, and rinsed onto a thin pad of silica. The crude product was eluted using 5:1 hexane:DCM, and solvent was removed on a rotary evaporator. The resulting blue oil was taken up in hexane and rinsed onto a thick pad of silica. Additional hexane was rinsed through the silica to elute excess acetylene, and then the product was eluted using 5:1 hexane:DCM. Removal of solvent yielded 0.11 g of blue oil, which was recrystallized from acetone (~8 mL) to yield 0.025 g (0.024 mmol, 2% relative to quinone) of blue plates. Analysis of the product provided the following data: $^1$H-NMR (400 MHz, $CDCl_3$) δ=9.0 (s, 4H), 7.7 (s, 4H), 2.6 (m, 4H), 2.5 (s, 12H), 1.3 (m, 28H), 1.2 (m, 4H).

Example 21

Synthesis of 6,13-Bis(3,3,4,4,5,5,6,6,7,7,8,8,9,9,10,10,10-heptadecafluorodecyldiisopropylsilylethynyl)-2-pentafluoroethylpentacene Synthesis of 1,2-Dimethyl-4-pentafluoroethylbenzene Into a nitrogen purged, flame dried round bottom flask was added 4-iodo-o-xylene (15.0 g, 64.7 mmol), sodium pentafluoropropionic acid (16.8 g, 90.5 mmol), copper (I) iodide (12.3 g, 64.6 mmol) and 100 mL of anhydrous N-methylpyrrolidinone. The reaction mixture was heated at 170° C. for 16 hours, then cooled to room temperature, and run through a thick silica gel plug with hexane. The collected yellow liquids were then evaporated to dryness on a rotary evaporator, and the oil distilled at 60° C. ($10^{-1}$ Torr) to collect the desired product (9.14 g, 63%) as a colorless liquid. Analysis of the product provided the following data: $^1$H NMR (200 MHz, $CDCl_3$) δ=2.347 (s, 6H), 7.247 (d, J=7.8 Hz, 1H), 7.357 (s, 1H), 7.401 (s, 1H). $^{13}$C NMR (50 MHz, $CDCl_3$) δ=19.810, 19.840, 124.013 (t, J=6.1 Hz), 127.472 (t, J=6.1 Hz), 130.158, 137.563, 141.205. GC-MS: m/z: 224 ($C_{10}H_9F_5$).

Synthesis of 1,2-Bis-bromomethyl-4-pentafluoroethylbenzene, 1-Bromomethyl-2-dibromomethyl-4-pentafluoroethylbenzene, and 1,2-Bis-dibromomethyl-4-pentafluoroethylbenzene Into a nitrogen purged, flame dried two neck round bottom flask was added 9.14 g (40.8 mmol) of 1,2-dimethyl-4-pentafluoroethylbenzene and 36.3 g (204 mmol) of N-bromosuccinimide. 1,2-Dichloroethane (200 mL) was added as well as a catalytic amount of AIBN. The reaction was heated at reflux (75° C.) for 16 hours. The reaction mixture was then cooled and filtered through a thin pad of silica gel, while washing with 1:1 dichloromethane:hexane. 28.2 g of liquid product was collected, and shown to be a mixture of brominated 2-pentafluoroethyl-o-xylenes by GC/MS. The brominated product mixture was used in the next step without further purification. Analysis of the brominated product mixture provided the following data: GC-MS: m/z: 382 ($C_{10}H_7Br_2F_5$), 379 ($C_{10}H_6Br_3F_5^+$—Br), 420 ($C_{10}H_5Br_4F_5^+$–Br,-2F), Synthesis of 2-Pentafluoroethylpentacene-6,13-dione Into a nitrogen purged round bottom flask was added 1,4-anthraquinone (8.50 g, 40.9 mmol) and approximately 40 mmol of the mixture of brominated 2-pentafluoroethyl-o-xylenes. Purged dimethylformamide (30 mL) was added to the flask under nitrogen and the reactants heated to 90° C. Potassium iodide (45.4 g, 274 mmol) was then slowly added to the reaction, and the temperature was raised to 130° C. The reaction mixture was stirred for 32 hours, then cooled to room temperature, the solids filtered and washed with acetone, followed by copious amounts of THF and diethyl ether. The insoluble yellow solid was then allowed to air dry for several hours to yield 5.9 g (34%) of product. Analysis of the product provided the following data: MS (EI 70 eV) m/z 426 (100%, $M^+$).

Synthesis of 6,13-Bis(3,3,4,4,5,5,6,6,7,7,8,8,9,9,10,10,10-heptadecafluorodecyldiisopropylsilylethynyl)-2-pentafluoroethylpentacene (3,3,4,4,5,5,6,6,7,7,8,8,9,9,10,10,10-heptadecafluorodecyldiisopropylsilyl)acetylene (1.5 g, 2.6 mmol) from Example 15 was added to an oven-dried round bottom flask and dissolved in hexane (18 mL). After cooling to 0° C., the solution was treated with n-butyllithium (0.8 mL, 2.0 mmol, 2.5 M in hexane) dropwise, and stirring was continued for 1 hr. 2-Pentafluoroethylpentacene-6,13-dione (0.26 g, 0.61 mmol) was added, and stirring was continued for 15 hr. Anhydrous THF (10 mL) was added, the reaction was allowed to continue for 1 hr, and then quenched by the addition of saturated ammonium chloride solution (10 mL). Reaction grade THF (10 mL), stannous chloride dihydrate (2 g), and 10% HCl (10 mL) were added, and the solution was stirred vigorously for 30 min. Hexane (20 mL) was added and the organic layer was separated, washed with 10% HCl (2×10 mL) and water (2×10 mL), dried over $MgSO_4$, and rinsed through a thin pad of silica (5:1 hexane:DCM). After removal of solvent, the blue oil was taken up in hexane, rinsed onto a thick pad of silica, and rinsed with more hexane (200 mL) to elute excess acetylene. The product was eluted using 9:1 hexane:DCM, and the solvent removed to yield the pure product as a blue liquid that very slowly solidified (0.16 g, 0.10 mmol, 17% from quinone). Analysis of the product provided the following data: $^1$H-NMR (400 MHz, $CDCl_3$) δ=9.3 (s, 1H), 9.3 (s, 1H), 9.2 (s, 1H), 9.2 (s, 1H), 8.2 (s, 1H), 8.1 (d, J=9.2 Hz, 1H), 7.9 (dd, J=6.8 Hz, 3.2 Hz, 2H), 7.5 (s, 1H), 7.5 (s, 1H), 7.4 (dd, J=6.8 Hz, 3.2 Hz, 1H), 2.5 (s, 4H), 1.4 (m, 28H), 1.2 (m, 4H).

Example 22

Preparation of Thin Film Transistors by Knife Coating Solution of 6,13-Bis(3,3,4,4,5,5,6,6,7,7,8,8,9,9,10,10,10-heptadecafluorodecyldiisopropylsilylethynyl)-pentacene Onto Cured Trimethylolpropane Triacrylate Gate Dielectric Layer 6,13-Bis(3,3,4,4,5,5,6,6,7,7,8,8,9,9,10,10,10-heptadecafluorodecyldiisopropylsilylethynyl)pentacene (0.0269 g) from Example 15 was added to a glass vial, and then 3-(trifluoromethyl)anisole (1.4713 g) was added to the vial. The vial was capped, and then wrapped with aluminum foil to shield the composition from light. The vial stood for a couple of hours and then was placed on an IKA LABORTECHNIK HS501 shaker (IKA Werke GmbH & Co. KG (Staufen, Germany)) and shaken for approximately 48 hours. The contents of the vial were filtered through a polytetrafluoroethylene (PTFE) filter with a pore size of 0.2 micron and 25 mm diameter that is commercially available under the trade designation ACRODISC® CR from Pall Life Sciences (East Hills, N.Y.) to afford an organic semiconductor solution.

Trimethylolpropane triacrylate (16.9992 g, SARTOMER™ SR-351) and 1-hydroxycyclohexylphenyl ketone (2.9959 g, IRGACURE™ 184) were placed in an amber glass jar with magnetic stir bar, the jar capped, and contents stirred until the 1-hydroxycyclohexylphenyl ketone dissolved. 3.9931 g of this solution and 15.9678 g of 3,5,5-trimethyl-2-cyclohexen-1-one (also named isophorone and available from Alpha Aesar, Ward Hill, Mass. USA) were added to a separate amber glass jar with magnetic stir bar, the jar capped, and contents stirred to provide a gate dielectric formulation.

A n-type silicon wafer (10.16 cm (4 in) diameter) with thermal oxide (i.e., a silicon <100> wafer highly doped n+ (arsenic) with a resistivity of less than 0.005 ohm-cm, and supplied with a 1000 Angstrom thermal oxide ($SiO_2$) on the front surface and coated with 100 Angstrom titanium nitride and 5000 Angstrom aluminum on the back surface) from Noel Technologies, Inc. (Campbell, Calif.) was cleaned using an oxygen plasma. The wafer was treated for 3 minutes in a Plasma Cleaning System (Model YES-G1000 from Yield Engineering Systems, Inc. (Livermore, Calif.)) using a power setting of 500 W and oxygen flow of 1 standard cubic centimeter per minute (sccm). The plasma-cleaned wafer was allowed to cool for a few minutes after cleaning to insure it was at room temperature, then the gate dielectric formulation was spin-coated onto the thermal oxide surface of the wafer at 2000 rpm for 1 min at a ramp rate of 432 rpm/s. The coated substrate was placed on a hotplate, which was preheated to 100° C., for 10 min. Then, the substrate was moved to a nitrogen-purged UV-irradiation chamber (254 nm germicidal lamp) where the coated dielectric was irradiated for 10 min. (dose=1.2 Joule/$cm^2$). After UV irradiation, the substrate was placed on a hotplate, which was preheated to 100° C., for 10 min. The substrate was removed from the hotplate and allowed to cool to room temperature. The thickness of the cured trimethylolpropane triacrylate gate dielectric layer was approximately 548 Angstroms. The gate dielectric was a composite of the cured trimethylolpropane triacrylate layer and the 1000 Angstrom thick thermal oxide ($SiO_2$) layer. The substrate was cleaved into approximately sixths to yield a piece for the coating of the organic semiconductor solution.

The knife coater blade (i.e., knife coater was Gardco Microm Applicator, Paul N. Gardner Company, Inc., Pompano Beach, Fla. USA) was placed approximately 305 microns (0.012 inches) above the surface of the cured trimethylolpropane triacrylate layer on the piece of silicon wafer, and a disposable glass pipette was used to place a small bead of the semiconductor solution between the blade and the surface. The knife coater was then drawn by hand over the wafer to coat the wafer with the semiconductor solution Immediately after knife coating the semiconductor solution, the solution-coated wafer was covered with a glass petri dish (approximately 90 mm diameter×15 mm deep) to slow the solvent, 3-(trifluoromethyl)anisole, evaporation. The sample was left to dry at room temperature in the dark.

After approximately 3 hours, the sample was dry. Gold source and drain electrodes (approximately 1000 Angstroms thick) were vapor deposited through a shadow mask onto the semiconductor layer using a thermal evaporator, thus forming transistors with a bottom gate, top contact architecture. The channel length was approximately 100 micrometers and channel width approximately 1000 micrometers. The mobilities of 10 transistors in which crystalline or semicrystalline pentacene covered the entire or almost entire channel region were determined by Mobility Value Test Method I and the average was $7.74 \times 10^{-3}$ $cm^2$/V-s.

Example 23

Preparation of Thin Film Transistors by Knife Coating Solution of 6,13-Bis((3,3,4,4,5,5,6,6,7,7,8,8,9,10,10,10-hexadecafluoro-9-trifluoromethldecyl)diisopropylsilylethynyl)-pentacene Onto $SiO_2$ Gate Dielectric Layer 6,13-Bis((3,3,4,4,5,5,6,6,7,7,8,8,9,10,10,10-hexadecafluoro-9-trifluoromethyldecyl)-diisopropylsilylethynyl)pentacene (0.0271 g) from Example 16 was added to a glass vial, and then 3-(trifluoromethyl)anisole (1.4719 g) was added to the vial. The vial was capped, and then wrapped with aluminum foil to shield the composition from light. The vial stood for a couple of hours and then was placed on an IKA LABORTECHNIK HS501 shaker (IKA Werke GmbH & Co. KG (Staufen, Germany)) and shaken for approximately 48 hours. The contents of the vial were filtered through a polytetrafluoroethylene (PTFE) filter with a pore size of 0.2 micron and 25 mm diameter that is commercially available under the trade designation ACRODISC® CR from Pall Life Sciences (East Hills, N.Y.).

A piece of n-type silicon wafer with thermal oxide (i.e., a 10.16 cm (4 inch) diameter silicon <100> wafer, which was highly doped n+ (arsenic) with a resistivity of <0.005 ohm-cm and supplied with a 1000 Angstrom thermal oxide ($SiO_2$) on the front surface and coated with 100 Angstrom TiN and 5000 Angstrom aluminum on the back surface from Noel Technologies, Inc. (Campbell, Calif.) was cleaved approximately into sixths to yield the piece) was treated for 4 minutes in a Plasma Cleaning System (Model YES-G1000 from Yield Engineering Systems, Inc. (Livermore, Calif.)) using a power setting of 500 Watts and oxygen pressure of approximately 200 milli-Torr prior to knife coating of the semiconductor solution.

The knife coater blade was placed approximately 305 microns (0.012 inches) above the thermal oxide surface of the piece of silicon wafer, and a disposable glass pipette was used to place a small bead of the semiconductor solution between the blade and the thermal oxide surface. The knife coater was then drawn by hand over the wafer to coat the wafer with the semiconductor solution Immediately after knife coating the semiconductor solution, the solution-coated wafer was covered with a glass petri dish (approximately 90 mm diameter× 15 mm deep) to slow the solvent, 3-(trifluoromethyl)anisole, evaporation. The sample was left to dry at room temperature in the dark.

After approximately 3 hours, the sample was dry. Gold source and drain electrodes (approximately 1000 Angstroms thick) were vapor deposited through a shadow mask onto the semiconductor layer using a thermal evaporator, thus forming transistors with a bottom gate, top contact architecture. The channel length was approximately 100 micrometers and channel width approximately 1000 micrometers. The mobilities of 7 transistors in which crystalline or semicrystalline pentacene covered the entire or almost entire channel region were determined by Mobility Value Test Method I and the average was $1.46 \times 10^{-3}$ cm$^2$/V-s.

Example 24

Pentacene Solution Stability to Ultraviolet (UV) Light 6,13-bis(triisopropylsilylethynyl)pentacene (TIPS, prepared essentially as described in U.S. Pat. No. 6,690,029 Anthony et al.), 6,13-bis(3,3,3-trifluoropropyldiisopropylsilylethynyl)pentacene (CF3), 6,13-bis(3,3,4,4,5,5,5-heptafluoropentyldiisopropylsilylethynyl)pentacene (C3F7), 6,13-bis(3,3,4,4,5,5,6,6,6-nonafluorohexyldiisopropylsilylethynyl)pentacene (C4F9), 6,13-bis(3,3,4,4,5,5,6,6,7,7,8,8,8-tridecafluorooctyldiisopropylsilylethynyl)pentacene (C6F13), and 6,13-bis(3,3,4,4,5,5,6,6,7,7,8,8,9,9,10,10,10-heptadecafluorodecyldiisopropylsilylethynyl)pentacene (C8F17) were weighed into separate glass vials, and toluene (EMD Chemicals, Inc., Gibbstown, N.J. USA, OmniSolv High Purity Solvent suitable for spectrophotometry) was weighed into the vials to afford $7.61 \times 10^{-5}$ M (molar) solutions. The vials were capped, wrapped with aluminum foil, and placed in the dark for approximately 16 hours to ensure dissolution of the pentacenes. All solutions were blue in color. Approximately 2.0 g of each pentacene solution was placed in separate UV-Visible spectrophotometer quartz cells. The cells (RF-3010-T cells from Spectrocell Inc., Oreland, Pa. USA) were 10×10 mm (path length=10 mm) with a volume of 3.5 ml and spectral range or window of 170 to 2200 nm. UV-Visible spectra of the pentacenes in solution at a temperature of 23° C. were obtained on an Agilent 8453 Diode Array Spectrometer (Agilent Technologies, Santa Clara, Calif. USA, Part Number G11038). UV-Visible spectra were obtained in Absorbance mode from 190 to 830 nm in 1 nm intervals and with an integration time of 5 seconds. All spectra were very similar.

The solutions were then irradiated with UV light for a total time of 90 minutes. The UV light was provided by two 15 Watt (W) blacklight bulbs (Sylvania GTE 350 Blacklight F15T8/350BL bulbs) in a lamp housing (Blak-Ray Lamp, Model XX-15L, UVP, Upland, Calif. USA). An envisioned plane tangent to the periphery of both of the two blacklight bulbs was held approximately parallel to the closest face of the UV-Visible cell, and the distance between this plane and the closest face of the cell was approximately 70 mm. The intensity of the UV radiation at the cell was approximately 5.27 mW/cm$^2$. UV-Visible spectra of the pentacenes in solution were obtained at different times (approximately every 15 min) during the UV irradiation. The solutions gradually diminished in the intensity of their blue color and took on a yellow tone, which was due to the decomposition of the pentacene.

Figure 5:
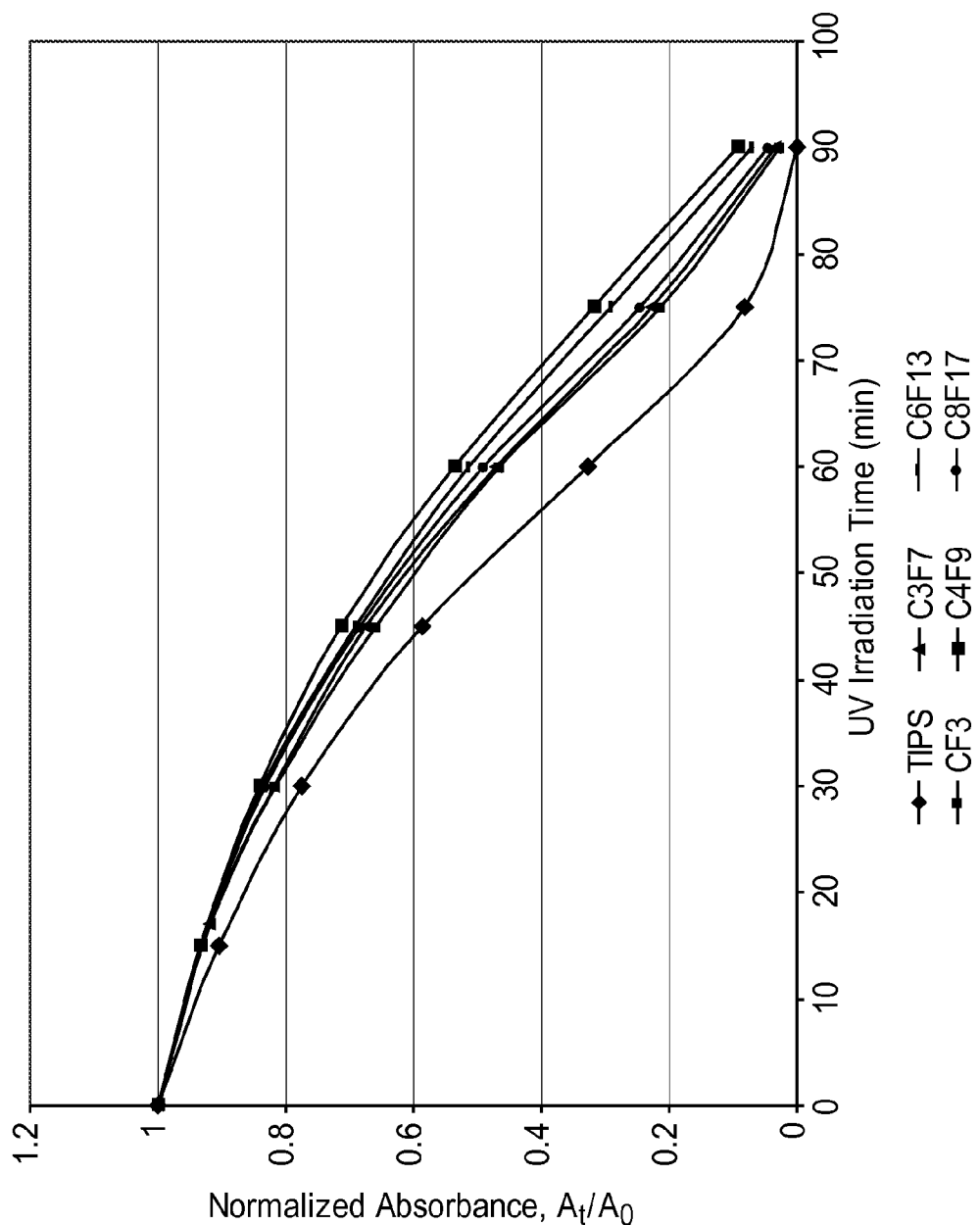
FIG. 5 is a representative plot of normalized absorbance ($A_t/A_o$) associated with the absorbance maximum at approximately 643 to 645 nanometers for various fluorinated pentacene compounds of the present invention compared to TIPS-pentacene in solution as a function of the time the solutions were irradiated with ultraviolet (UV) light.

Absorbance at the absorption maxima at 643 to 645 nanometers (nm) was monitored with UV irradiation time for all the pentacenes. The absorbance decreased with time, which was reflective of the decomposition of the pentacene with UV irradiation. The normalized absorbance, $A_t/A_0$, i.e. the absorbance after UV irradiation time, t, divided by the absorbance prior to UV irradiation, $A_0$ or absorbance at t=0, for each pentacene is plotted as shown in FIG. 5. The rate of decrease of the normalized absorbance with UV irradiation time was the greatest for 6,13-bis(triisopropylsilylethynyl) pentacene, which indicates the greater stability of the pentacenes with the fluoroalkyl-substituted silylethynyl groups to UV light.

Example 25

Preparation of Thin Film Transistors by Knife Coating Solution of 6,13-Bis(3,3,4,4,5,5,6,6,7,7,8,8,9,9,10,10,10-heptadecafluorodecyldiisopropylsilylethynyl)-2,3,9,10-tetramethylpentacene Onto SiO$_2$ Gate Dielectric Layer 6,13-Bis(3,3,4,4,5,5,6,6,7,7,8,8,9,9,10,10,10-heptadecafluorodecyldiisopropylsilylethynyl)-2,3,9,10-tetramethylpentacene (0.0178 g) from Example 17 was added to a glass vial, and then 3-(trifluoromethyl)anisole (0.9868 g) was added to the vial. The vial was capped, and then wrapped with aluminum foil to shield the composition from light. The vial stood for approximately 22 hours and then was placed on an IKA LABORTECHNIK HS501 shaker (IKA Werke GmbH & Co. KG (Staufen, Germany)) and shaken for approximately 48 hours. Not all of the pentacene that was added to the vial dissolved. The contents of the vial were filtered through a polytetrafluoroethylene (PTFE) filter with a pore size of 0.2 micron and 25 mm diameter that is commercially available under the trade designation ACRODISC® CR from Pall Life Sciences (East Hills, N.Y.).

Thin film transistors were fabricated and tested in the same manner as described in Example 23, except the 6,13-Bis(3,3,4,4,5,5,6,6,7,7,8,8,9,9,10,10,10-heptadecafluorodecyldiisopropylsilylethynyl)-2,3,9,10-tetramethylpentacene in 3-(trifluoromethyl)anisole solution was used. The average mobility of 12 transistors was $8.45 \times 10^{-3}$ cm$^2$/V-s.

Example 26

Preparation of Thin Film Transistors by Knife Coating Solution of 6,13-Bis(3,3,4,4,5,5,6,6,6-nonafluorohexyldiisopropylsilylethynyl)-2,3,9,10-tetramethylpentacene Onto SiO$_2$ Gate Dielectric Layer 6,13-Bis(3,3,4,4,5,5,6,6,6-nonafluorohexyldiisopropylsilylethynyl)-2,3,9,10-tetramethylpentacene (0.0115 g) from Example 20 was added to a glass vial, and then 3-(trifluoromethyl)anisole (0.6293 g) was added to the vial. The vial was capped, and then wrapped with aluminum foil to shield the composition from light. The vial stood for 22 hours and then was placed on an IKA LABORTECHNIK HS501 shaker (IKA Werke GmbH & Co. KG (Staufen, Germany)) and shaken for approximately 48 hours. Not all of the pentacene that was added to the vial dissolved. The contents of the vial were filtered through a polytetrafluoroethylene (PTFE) filter with a pore size of 0.2 micron and 25 mm diameter that is commercially available under the trade designation ACRODISC® CR from Pall Life Sciences (East Hills, N.Y.).

Thin film transistors were fabricated and tested in the same manner as described in Example 23, except the 6,13-Bis(3,3,4,4,5,5,6,6,6-nonafluorohexyldiisopropylsilylethynyl)-2,3,9,10-tetramethylpentacene in 3-(trifluoromethyl)anisole solution was used. The average mobility of 9 transistors was $1.20 \times 10^{-2}$ cm$^2$/V-s.

Example 27

Synthesis of 6,13-bis((N-methyl-nonafluorobutylsulfonamidopropyl)diisopropylsilylethynyl)pentacene Synthesis of N-Allyl-N-methylnonafluorobutanesulfonamide A mixture of 313 g (1 mol) N-methylnonafluorobutanesulfonamide (3M Co., U.S. Pat. No. 6,664,354, Savu), 216 g (1 mol) 25% sodium methoxide in methanol (Aldrich), and 100 mL THF (EMD) was stirred at 50° C. for one hour and stripped. The residue was diluted with 600 mL THF and treated with 100 mL (1.15 mol) allyl bromide (Aldrich). The mixture was stirred at 40° C. for about 8 hr and then diluted with water. Extraction with methylene chloride and distillation yielded 321.7 g colorless liquid, by 75-80° C./1.1 mm Hg.

Synthesis of 3-(N-methylnonafluorobutane-sulfonamido)propyl)diisopropylsilyl chloride N-Allyl-N-methylnonafluorobutanesulfonamide (3.53 g, 0.01 mol), 1.51 g (0.01 mol) diisopropylchlorosilane (also referred to herein as diisopropylsilyl chloride, Alfa Aesar), and 0.4 g platinum(0)-1,3-divinyl-1,1,3,3-tetramethyldisiloxane complex (18% in toluene, 3M supplied, but same compound in xylene available from Sigma-Aldrich) were mixed and warmed at about 60° C. for 1.5 hr. Short-path distillation provided a main cut at 105° C./0.1 mm Hg, proven by GC/MS to be predominantly the desired product (mass 503), accompanied by some mass 780, corresponding to the replacement of Cl by $NMeSO_2C_4F_9$. Scale-up to 35.3 g (0.1 mol) N-allyl-N-methylnonafluorobutanesulfonamide, 15.1 g (0.1 mol) diisopropylchlorosilane, and 4.0 g platinum(0)-1,3-divinyl-1,1,3,3-tetramethyldisiloxane complex and one-plate distillation of the resulting 49.7 g after 24 hr gave 23.4 g of by 130-185/1 mm Hg, approximately equal amounts of both components by GLC.

Synthesis of 3-(N-methylnonafluorobutane-sulfonamido)propyl)diisopropylsilyl acetylene An oven dried 500 mL round bottom flask with nitrogen atmosphere was charged with hexane (100 mL), tetrahydrofuran (20 mL), and trimethylsilylacetylene (4.8 g, 48.9 mmol) and cooled with an ice bath. N-butyllithium (2.5 M in hexane, 19.4 mL) was added dropwise and the reaction mixture was allowed to warm to room temperature. The reaction product (20.0 g) from the previously described step, "Synthesis of 3-(N-methylnonafluorobutanesulfonamido)propyl) diisopropylsilyl chloride," was slowly added and the contents allowed to stir for sixteen hours. Water was added slowly (100 mL) and the mixture was stirred vigorously. The organic layer was separated, and the water layer extracted with 100 mL of hexane. The organic layers were combined and concentrated under reduced pressure to a brown oil. The oil was purified using chromatography on silica gel with hexane as an eluant, resulting in 23.9 g of the trimethylsilyl-protected acetylene as a clear oil. The oil (23.9 g, 42.2 mmol) was charged to an oven dried 500 mL round bottom flask. Methanol (50 mL), tetrahydrofuran (50 mL), and 5% aqueous NaOH (1 mL) were added to the flask and then stirred for one hour. Water (100 mL) was then added, and stirred vigorously. The organic layer was separated, and the aqueous layer was extracted two times with hexane (2×100 mL). The organic layers were combined and concentrated under reduced pressure to yield 3-(N-methyl-nonafluorobutanesulfonamido)propyl)diisopropylsilyl acetylene as a clear oil (11.2 g, 54%).

Synthesis of 6,13-bis((N-methyl-nonafluorobutylsulfonamidopropyl)diisopropylsilylethynyl)pentacene An oven dried 500 mL round bottom flask with nitrogen atmosphere was charged with 3-(N-methylnonafluorobutanesulfonamido)propyl)diisopropylsilyl acetylene (11.2 g, 22.7 mmol) and hexane (100 mL). This was cooled with an ice bath and n-butyllithium (2.5M in hexane, 7.6 mL) was added dropwise. The reaction mixture was allowed to warm to room temperature. 6,13-pentacenequinone (2.1 g, 6.8 mmol) was added to the reaction mixture and this was allowed to stir for sixteen hours. Tetrahydrofuran was added (80 mL) and the mixture was allowed to stir for six days. Saturated ammonium chloride (60 mL) was added, followed by stannous chloride dihydrate (16 g, 70.9 mmol) and 10% aqueous HCl (60 mL). The round bottom flask was covered with aluminum foil to keep out light. The reaction mixture was stirred vigorously for one hour, and then the organic layer was separated, and washed with 10% aqueous HCl (2×60 mL) followed by 60 mL of water. The organic layer was then dried with $MgSO_4$, filtered, and then concentrated under reduced pressure to a brown oil. The oil was purified by chromatography on silica gel with dichloromethane in hexane as an eluant to obtain 6,13-bis((N-methylnonafluorobutylsulfonamidopropyl)diisopropylsilylethynyl)pentacene as a dark blue solid (473 mg, 2%). Analysis of the product in deuterated chloroform, spiked with a small amount of 1,4-bis-trifluoromethylbenzene as a cross-reference standard, provided the following data: $^1$H-NMR (500 MHz, $CDCl_3$) δ: 9.23-9.31 (m, 4H), 7.95-8.02 (m, 4H), 7.41-7.47 (m, 4H), 3.70-3.87 (m, 2H), 3.22-3.39 (m, 2H), 3.01-3.05 (m, 6H), 2.02-2.15 (m, 4H), 1.31-1.41 (m, 24H), 1.01-1.10 (m, 4H), 0.94-1.01 (m, 4H); $^{19}$F NMR (470 MHz, $CDCl_3$) δ ppm −126.99−−126.11 (m, 2F), −121.96 (dd, J=9.34 Hz, 4.00 Hz, 2F), −112.48 (broad s, 2F), −82.00−−80.80 (m, 3F).

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:
1. A pentacene compound having a chemical structure:

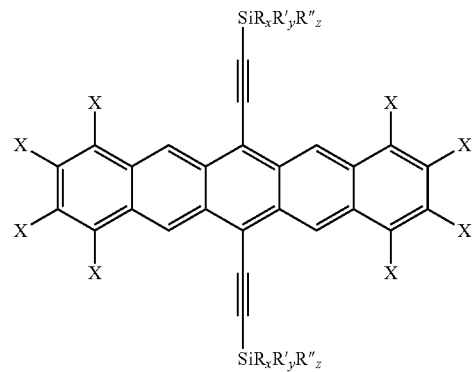

wherein:
   each R, R' and R" independently comprises (i) hydrogen, (ii) a branched or unbranched, substituted or unsubstituted alkyl group, (iii) a branched or unbranched, substituted or unsubstituted alkenyl group, (iv) a substituted or unsubstituted cycloalkyl group, (v) a substituted or unsubstituted cycloalkylalkylene group, (vi) a branched or unbranched, substituted or unsubstituted alkynyl group, (vii) a substituted or unsubstituted aryl group, (viii) a substituted or unsubstituted arylalkylene group, (ix) an acetyl group, (x) a substituted or unsubstituted heterocyclic ring comprising at least one of O, N, S and Se in the ring, (xi) a substituted or unsubstituted ether group or polyether group, or (xii) a substituted or unsubstituted sulfonamide group; and at least one of R, R' and R" is present and comprises a fluorinated monovalent radical comprising the branched or unbranched substituted alkyl group, the branched or unbranched substituted alkenyl group, the substituted cycloalkyl group, the substituted cycloalkylalkylene group, the branched or unbranched substituted alkynyl group, the substituted aryl group, the substituted arylalkylene group, the substituted heterocyclic ring comprising at least one of O, N, S and Se in the ring, the substituted ether group or polyether group, or the substituted sulfonamide group, said fluorinated monovalent radical comprising one or more fluorine atoms with said one or more fluorine atoms being separated from both silicon atoms by at least three atoms or at least four covalent bonds;

x, y and z each independently equal 0, 1, 2 or 3;

(x+y+z)=3; and each X independently comprises (i) hydrogen, (ii) a halogen, (iii) a branched or unbranched, substituted or unsubstituted alkyl group, (iv) a substituted or unsubstituted aryl group, (v) a branched or unbranched, substituted or unsubstituted alkenyl group, (vi) a branched or unbranched, substituted or unsubstituted alkynyl group, (vii) a cyano group, (viii) a nitro group, (ix) a branched or unbranched, substituted or unsubstituted alkoxy group, or (x) any two adjacent X groups combine to form (a) a substituted or unsubstituted carbocyclic ring or (b) a substituted or unsubstituted heterocyclic ring.

2. The pentacene compound of claim 1, wherein R, R' and R" together comprise two identical groups and one dissimilar group.

3. The pentacene compound of claim 1, wherein said fluorinated monovalent radical comprises (i) a branched or unbranched, fluorinated C3-C18 alkyl group, (ii) a branched or unbranched, fluorinated C3-C18 alkenyl group, (iii) a fluorinated cycloalkyl group, (iv) a fluorinated cycloalkylalkylene group, (v) a branched or unbranched, fluorinated C3-C18 alkynyl group, (vi) a fluorinated aryl group, or (vii) a fluorinated arylalkylene group.

4. The pentacene compound of claim 1, wherein said fluorinated monovalent radical comprises —CH$_2$CH$_2$R$_f$ and R$_f$ is a partially or completely fluorinated C1-C16 alkyl group.

5. The pentacene compound of claim 1, wherein said fluorinated monovalent radical comprises:

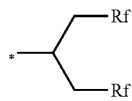

and each R$_f$ is independently a partially or completely fluorinated alkyl group having up to four carbon atoms.

6. The pentacene compound of claim 1, wherein said fluorinated monovalent radical comprises:

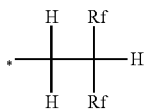

and each R$_f$ is independently a partially or completely fluorinated alkyl group having up to four carbon atoms.

7. The pentacene compound of claim 1, wherein at least one atom of said at least three atoms comprises an atom other than carbon.

8. The pentacene compound of claim 1, wherein said fluorinated monovalent radical comprises (i) a branched or unbranched, fluorinated ether group or polyether group, or (ii) a branched or unbranched, fluorinated sulfonamide group.

9. The pentacene compound of claim 1, wherein R, R' and R" together comprise (i) at least one of said fluorinated monovalent radical in combination with (ii) at least one C1-C8 alkyl groups, (iii) at least one C2-C8 alkenyl groups, (iv) at least one C3-C8 cycloalkyl groups, or (v) a C1 to C8 alkyl group in combination with a C3-C8 cycloalkyl group or a C2-C8 alkenyl group.

10. The pentacene compound of claim 1, wherein R, R' and R" together comprise (i) at least one fluorinated monovalent radical in combination with (ii) two C1 to C8 alkyl groups, (iii) two C3-C8 cycloalkyl groups, or (iv) two C2-C8 alkenyl groups.

11. The pentacene compound of claim 1, wherein R, R' and R" together comprise (i) at least one of said fluorinated monovalent radical in combination with (ii) at least one isopropyl group, (iii) at least one isopropenyl group, or (iv) an isopropyl group and an isopropenyl group.

12. The pentacene compound of claim 1, wherein each X independently comprises (i) hydrogen, (ii) a halogen, (iii) a branched or unbranched, substituted or unsubstituted alkyl group, (iv) a cyano group, or (v) a branched or unbranched, substituted or unsubstituted alkoxy group.

13. The pentacene compound of claim 1, wherein at least one X comprises (i) fluorine, (ii) an alkyl group, or (iii) a perfluoroalkyl group.

14. The pentacene compound of claim 1, wherein at least one X comprises (i) fluorine, (ii) a methyl group, or (iii) a trifluoromethyl group.

15. A composition comprising the pentacene compound of claim 1, wherein the composition further comprises a solvent.

16. The composition of claim 15, wherein said solvent comprises a fluorinated solvent.

17. The composition of claim 16, wherein the composition further comprises (i) a non-fluorinated organic solvent, (ii) an additional fluorinated liquid, (iii) a surfactant, or (iv) any combination of (i) to (iii).

18. The composition of claim 15, further comprising a polymer.

19. A substrate having at least one coatable surface and a coated layer on said at least one coatable surface, wherein said coated layer comprises the pentacene compound of claim 1.

20. An electronic device comprising a semiconductor layer, said semiconductor layer comprises the pentacene compound of claim 1.

* * * * *

UNITED STATES PATENT AND TRADEMARK OFFICE
CERTIFICATE OF CORRECTION

PATENT NO. : 8,920,679 B2
APPLICATION NO. : 13/318617
DATED : December 30, 2014
INVENTOR(S) : Clough et al.

It is certified that error appears in the above-identified patent and that said Letters Patent is hereby corrected as shown below:

In The Specification

Column 29, line 66, delete "Alburquerque," and insert therefor -- Albuquerque, --, Column 31, line 5, delete "$I_{DS} = \mu WC(V_{Gs} - V_t)^2 \div 2L$" and insert therefor
-- $I_{DS} = \mu WC(V_{GS} - V_t)^2 \div 2L$ --, Column 40, lines 16-17, delete "tridecafluorooctyldfisopropylsilylethynyl)pentacene" and insert therefor -- tridecafluorooctyldiisopropylsilylethynyl)pentacene --, Column 40, lines 19-20, delete "tridecafluorooctyldfisopropylsilyflacetylene" and insert therefor -- tridecafluorooctyldiisopropylsilyl)acetylene --, Column 40, lines 56-57, delete "tridecafluorooctyldfisopropylsilyflacetylene" and insert therefor -- tridecafluorooctyldiisopropylsilyl)acetylene --, Column 41, line 3, delete "tridecafluorooctyldfisopropylsilyl)bromide" and insert therefor -- tridecafluorooctyldiisopropylsilyl)bromide --, Column 45, line 65, delete "H-NMR" and insert therefor -- $^1$H-NMR --, Column 46, line 55, delete "H-NMR" and insert therefor -- $^1$H-NMR --, Column 48, line 4, delete "-2F)," and insert therefor -- -2F). --, Column 49, line 60, delete "solution" and insert therefor -- solution. --, Column 50, line 15, delete "trifluoromethldecyl)" and insert therefor -- trifluoromethyldecyl) --, Column 50, line 53, delete "solution" and insert therefor -- solution. --, and Column 53, line 7, delete "by" and insert therefor -- bp --.

Signed and Sealed this
Nineteenth Day of January, 2016

Michelle K. Lee
*Director of the United States Patent and Trademark Office*